United States Patent
Hart et al.

(10) Patent No.: US 9,675,378 B2
(45) Date of Patent: Jun. 13, 2017

(54) STEERABLE KINK-RESISTANT SHEATH

(71) Applicant: Applied Medical Resources Corporation, Rancho Santa Margarita, CA (US)

(72) Inventors: Charles C. Hart, Rancho Santa Margarita, CA (US); John R. Brustad, Rancho Santa Margarita, CA (US); Nabil Hilal, Rancho Santa Margarita, CA (US); Henry Kahle, Corona, CA (US); Donald L. Gadberry, Capistrano Beach, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 597 days.

(21) Appl. No.: 14/164,954

(22) Filed: Jan. 27, 2014

(65) Prior Publication Data
US 2014/0296778 A1    Oct. 2, 2014

Related U.S. Application Data

(60) Continuation of application No. 12/950,782, filed on Nov. 19, 2010, now Pat. No. 8,721,826, which is a
(Continued)

(51) Int. Cl.
*A61B 17/34*    (2006.01)
*A61B 17/00*    (2006.01)
(Continued)

(52) U.S. Cl.
CPC .... *A61B 17/3421* (2013.01); *A61B 2017/003* (2013.01); *B29C 53/58* (2013.01);
(Continued)

(58) Field of Classification Search
CPC .......... A61B 17/3421; A61B 2017/003; A61B 2034/302; A61B 2017/00318; A61M 25/0147; A61M 25/0105; A61M 25/0138
See application file for complete search history.

(56) References Cited

U.S. PATENT DOCUMENTS 2,130,586 A    9/1938   Huston
2,688,329 A    9/1954   Wallace
(Continued)

FOREIGN PATENT DOCUMENTS

EP    0 421 650 A    4/1991
EP    0 605 796 A2    7/1994
(Continued)

OTHER PUBLICATIONS

International Searching Authority, International Search Report and the Written Opinion of the International Searching Authority for International application No. PCT/US07/69282, titled, Medical Tubing Having Variable Characteristics Using Thermal Winding, mailed Jan. 16, 2008.
(Continued)

*Primary Examiner* — Theodore Stigell
(74) *Attorney, Agent, or Firm* — Rimas T. Lukas

(57) ABSTRACT

A steerable kink resistant access device is provided having an elongated body and a steerable portion; methods for manufacturing the kink resistant device are also provided. The access sheath has an outside diameter sufficiently small so that it may be inserted into a body cavity or conduit. The access sheath typically has two internal lumen, a first lumen sized and configured as an access to a surgical site and a second lumen sized and configured to contain a tensioning device that, when acted upon, will deflect the steerable portion. The tensioning device may be directly or remotely
(Continued)

attached to an actuation device that operates to control the tensioning and loosening of the tensioning device.

20 Claims, 28 Drawing Sheets

Related U.S. Application Data continuation of application No. 11/695,449, filed on Apr. 2, 2007, now Pat. No. 7,850,811, which is a division of application No. 10/832,867, filed on Apr. 26, 2004, now abandoned, which is a continuation-in-part of application No. 10/766,138, filed on Jan. 28, 2004, now abandoned, and a continuation-in-part of application No. 10/298,116, filed on Nov. 15, 2002, now Pat. No. 7,005,026, and a continuation-in-part of application No. 10/766,138, filed on Jan. 28, 2004, now abandoned.

(60) Provisional application No. 60/465,310, filed on Apr. 25, 2003.

(51) Int. Cl.
  B29C 53/58    (2006.01)
  B29C 63/18    (2006.01)
  B29D 23/18    (2006.01)
  B29K 19/00    (2006.01)
  B29K 83/00    (2006.01)
  B29L 31/00    (2006.01)
  B32B 1/08     (2006.01)

(52) U.S. Cl.
  CPC ............. B29C 63/18 (2013.01); B29D 23/18 (2013.01); B29K 2019/00 (2013.01); B29K 2083/00 (2013.01); B29L 2031/7546 (2013.01); B32B 1/08 (2013.01)

(56) References Cited

U.S. PATENT DOCUMENTS

| | | |
|---|---|---|
| 2,688,343 A | 9/1954 | Cuddeback |
| 2,701,562 A | 2/1955 | Michael et al. |
| 2,722,263 A | 11/1955 | Beare et al. |
| 3,113,897 A | 12/1963 | Gisle Skansen et al. |
| 3,226,767 A | 1/1966 | Howell |
| 3,354,695 A | 11/1967 | Szente |
| 3,477,891 A | 11/1969 | Hawerkamp |
| 3,503,385 A | 3/1970 | Stevens |
| 3,585,707 A | 6/1971 | Stevens |
| 3,617,415 A | 11/1971 | Hawerkamp |
| 3,618,613 A | 11/1971 | Schulte |
| 3,910,808 A | 10/1975 | Steward |
| 3,919,026 A | 11/1975 | Mizutani et al. |
| 3,988,190 A | 10/1976 | McWilliams |
| 4,010,054 A | 3/1977 | Bradt |
| 4,051,844 A | 10/1977 | Chiulli |
| 4,078,957 A | 3/1978 | Bradt |
| 4,135,869 A | 1/1979 | Loyer |
| 4,302,261 A | 11/1981 | Simkins et al. |
| 4,343,672 A | 8/1982 | Kanao |
| 4,350,547 A | 9/1982 | Kanao |
| 4,466,854 A | 8/1984 | Hawerkamp |
| 4,470,941 A | 9/1984 | Kurtz |
| 4,540,360 A | 9/1985 | Leo |
| 4,586,923 A | 5/1986 | Gould et al. |
| 4,596,023 A | 6/1986 | Goulde et al. |
| 4,605,990 A | 8/1986 | Wilder et al. |
| 4,619,643 A | 10/1986 | Bai et al. |
| 4,690,175 A | 9/1987 | Ouchi et al. |
| 4,707,906 A | 11/1987 | Posey |
| 4,811,743 A | 3/1989 | Stevens |
| 4,818,460 A | 4/1989 | Nied |
| 4,820,274 A | 4/1989 | Choski et al. |
| 4,826,423 A | 5/1989 | Kemp et al. |
| 4,911,148 A | 3/1990 | Sosnowski et al. |
| 5,084,033 A | 1/1992 | O'Neill |
| 5,092,950 A | 3/1992 | Spoo et al. |
| 5,179,935 A | 1/1993 | Miyagi |
| 5,180,376 A | 1/1993 | Fischell et al. |
| 5,195,968 A | 3/1993 | Lundquist et al. |
| 5,228,441 A | 7/1993 | Lundquist |
| 5,254,088 A | 10/1993 | Lundquist et al. |
| H1261 H | 12/1993 | Gibson et al. |
| 5,273,535 A | 12/1993 | Edwards et al. |
| 5,275,151 A | 1/1994 | Shockey et al. |
| 5,284,128 A | 2/1994 | Hart |
| 5,304,131 A | 4/1994 | Paskar |
| 5,315,996 A | 5/1994 | Lundquist |
| 5,322,064 A | 6/1994 | Lundquist |
| 5,328,467 A | 7/1994 | Edwards et al. |
| 5,329,923 A | 7/1994 | Lundquist |
| 5,342,299 A | 8/1994 | Snoke et al. |
| D351,652 S | 10/1994 | Thompson et al. |
| 5,383,852 A | 1/1995 | Stevens-Wright |
| 5,395,327 A | 3/1995 | Lundquist et al. |
| 5,409,469 A | 4/1995 | Schaerf |
| 5,429,127 A | 7/1995 | Kolobow |
| 5,441,483 A | 8/1995 | Avitall |
| 5,456,664 A | 10/1995 | Heinzelman et al. |
| 5,462,527 A | 10/1995 | Stevens-Wright et al. |
| 5,472,435 A | 12/1995 | Sutton |
| 5,484,407 A | 1/1996 | Osypka |
| 5,507,751 A | 4/1996 | Goode |
| 5,509,910 A | 4/1996 | Lunn |
| 5,512,035 A | 4/1996 | Konstorum et al. |
| 5,531,687 A | 7/1996 | Snoke et al. |
| 5,531,721 A | 7/1996 | Pepin et al. |
| 5,558,737 A | 9/1996 | Brown et al. |
| 5,632,734 A | 5/1997 | Galel |
| 5,637,168 A | 6/1997 | Carlson |
| 5,702,433 A | 12/1997 | Taylor et al. |
| 5,709,665 A | 1/1998 | Vergano et al. |
| 5,774,950 A | 7/1998 | Stout |
| 5,792,116 A | 8/1998 | Berg et al. |
| 5,827,278 A | 10/1998 | Webster, Jr. |
| 5,836,925 A | 11/1998 | Soltesz et al. |
| 5,840,031 A | 11/1998 | Crowley |
| 5,848,986 A | 12/1998 | Lundquist et al. |
| 5,863,366 A | 1/1999 | Snow |
| 5,865,800 A | 2/1999 | Mirarchi et al. |
| 5,879,499 A | 3/1999 | Corvi |
| 5,888,436 A | 3/1999 | Keith et al. |
| 5,891,088 A | 4/1999 | Thompson et al. |
| 5,902,287 A | 5/1999 | Martin |
| 5,904,667 A | 5/1999 | Faiwell |
| 5,935,102 A | 8/1999 | Bowden et al. |
| 5,945,048 A | 8/1999 | Ensinger |
| 5,947,940 A | 9/1999 | Beisel et al. |
| 5,976,075 A | 11/1999 | Beane et al. |
| 5,984,907 A | 11/1999 | McGee et al. |
| 6,007,531 A | 12/1999 | Snoke et al. |
| 6,033,378 A | 3/2000 | Lundquist et al. |
| 6,045,547 A | 4/2000 | Ren |
| 6,146,355 A | 11/2000 | Biggs |
| 6,171,277 B1 | 1/2001 | Ponzi |
| 6,198,974 B1 | 3/2001 | Webster, Jr. |
| 6,203,732 B1 | 3/2001 | Clubb et al. |
| 6,246,914 B1 | 6/2001 | de la Rama |
| 6,263,224 B1 | 7/2001 | West |
| 6,306,235 B1 | 10/2001 | Henderson |
| 6,337,142 B2 | 1/2002 | Harder |
| 6,368,316 B1 | 4/2002 | Jansen et al. |
| 6,451,005 B1 | 9/2002 | Saitou et al. |
| 6,464,632 B1 | 10/2002 | Taylor |
| 6,485,455 B1 | 11/2002 | Thompson et al. |
| 6,500,167 B1 | 12/2002 | Webster, Jr. |
| 6,511,471 B2 | 1/2003 | Rosenman et al. |
| 6,533,770 B1 | 3/2003 | Lepulu et al. |
| 6,533,984 B2 | 3/2003 | Curti |
| 6,537,405 B1 | 3/2003 | Henderson et al. |

(56) References Cited

U.S. PATENT DOCUMENTS

| | | | |
|---|---|---|---|
| 6,540,734 B1 | 4/2003 | Chiu et al. | |
| 6,544,215 B1 | 4/2003 | Bencini et al. | |
| 6,599,265 B2 | 7/2003 | Bon | |
| 6,602,278 B1 | 8/2003 | Thompson et al. | |
| 6,605,171 B1 | 8/2003 | Debalme et al. | |
| 6,648,875 B2 | 11/2003 | Simpson et al. | |
| 6,652,506 B2 | 11/2003 | Bowe et al. | |
| 6,663,588 B2 | 12/2003 | DuBois et al. | |
| 6,669,886 B1 | 12/2003 | Willard | |
| 6,716,207 B2 | 4/2004 | Farnholtz | |
| 6,776,765 B2 | 8/2004 | Soukup et al. | |
| 6,783,491 B2 * | 8/2004 | Saadat | A61B 1/0008 600/114 |
| 6,804,866 B2 | 10/2004 | Lemke et al. | |
| 6,836,687 B2 | 12/2004 | Kelley et al. | |
| D504,175 S | 4/2005 | Westbrook | |
| 6,916,306 B1 | 7/2005 | Jenkins et al. | |
| 6,976,987 B2 | 12/2005 | Flores | |
| 6,979,312 B2 | 12/2005 | Shimada | |
| 7,005,026 B2 | 2/2006 | Brustad et al. | |
| 7,534,317 B2 | 5/2009 | Brustad et al. | |
| 7,850,811 B2 | 12/2010 | Hart et al. | |
| 2001/0010247 A1 | 8/2001 | Snow | |
| 2001/0037084 A1 | 11/2001 | Nardeo | |
| 2002/0022762 A1 | 2/2002 | Beane et al. | |
| 2002/0177789 A1 | 11/2002 | Ferry et al. | |
| 2003/0135199 A1 | 7/2003 | Rosenman et al. | |
| 2003/0149422 A1 | 8/2003 | Muller | |
| 2003/0163085 A1 | 8/2003 | Tanner et al. | |
| 2003/0199817 A1 | 10/2003 | Thompson et al. | |
| 2003/0201058 A1 | 10/2003 | Banas et al. | |
| 2003/0230822 A1 | 12/2003 | Bartholomew | |
| 2003/0230823 A1 | 12/2003 | Bartholomew | |
| 2003/0236493 A1 | 12/2003 | Mauch | |
| 2004/0010243 A1 | 1/2004 | Klint | |
| 2004/0097881 A1 | 5/2004 | Brustad et al. | |
| 2004/0215109 A1 | 10/2004 | Pingleton et al. | |
| 2005/0096590 A1 | 5/2005 | Gullickson et al. | |
| 2005/0131387 A1 | 6/2005 | Pursley | |
| 2005/0159728 A1 | 7/2005 | Armour et al. | |
| 2005/0165366 A1 | 7/2005 | Brustad et al. | |
| 2005/0197623 A1 | 9/2005 | Leeflang et al. | |
| 2005/0277851 A1 | 12/2005 | Whittaker et al. | |
| 2005/0277875 A1 | 12/2005 | Selkee | |
| 2005/0288627 A1 | 12/2005 | Mogul | |
| 2005/0288656 A1 | 12/2005 | Koemer et al. | |
| 2011/0005661 A1 | 1/2011 | Brustad et al. | |
| 2011/0066105 A1 | 3/2011 | Hart et al. | |

FOREIGN PATENT DOCUMENTS

| | | |
|---|---|---|
| JP | 405038325 A | 2/1993 |
| WO | WO 97/10749 A | 3/1997 |
| WO | WO 00/25849 A | 5/2000 |
| WO | WO 01/10492 | 2/2001 |
| WO | WO 03/015638 A | 2/2003 |

OTHER PUBLICATIONS

International Bureau of WIPO, International Preliminary Report on Patentability for International Application No. PCT/US07/69282, titled, Medical Tubing Having Variable Characteristics Using Thermal Winding, dated Nov. 18, 2008.

International Search Report and Written Opinion of the International Searching Authority for International Application No. PCT/US205/001129, titled, Medical Tubing Having Variable Characteristics and Method of Making Same, mailed Nov. 23, 2005, 20 pages.

International Bureau of WIPO, International Preliminary Report on Patentability for International Application No. PCT/US/2005/001129 dated Jul. 31, 2006.

International Bureau of WIPO, International Preliminary Report on Patentability for International Application No. PCT/US2004/01318,, titled "Steerable Kink Resistant Sheath". dated Mar. 27, 2006.

International Searching Authority, International Search Report and Written Opinion for PCT/US04/13118, titled, Steerable Kink-Resistant Sheath, mailed Mar. 8, 2006.

European Patent Office, Supplementary European Search Report for Application No. EP 04 75 0825, based on International Application No. PCT/US2004/013118, titled, Steerable Kink-Resistant Sheath, dated Oct. 2, 2006.

\* cited by examiner

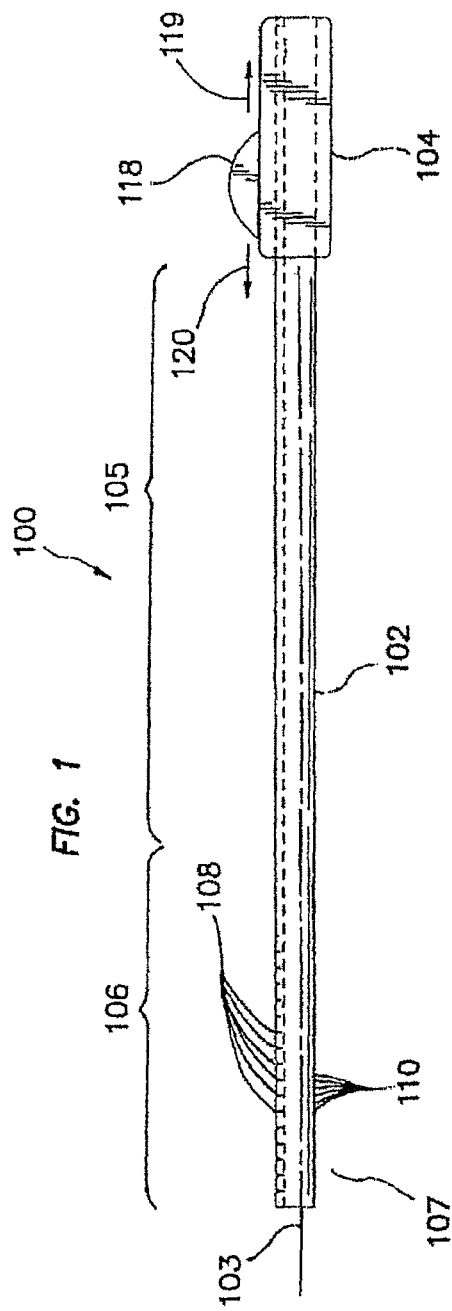
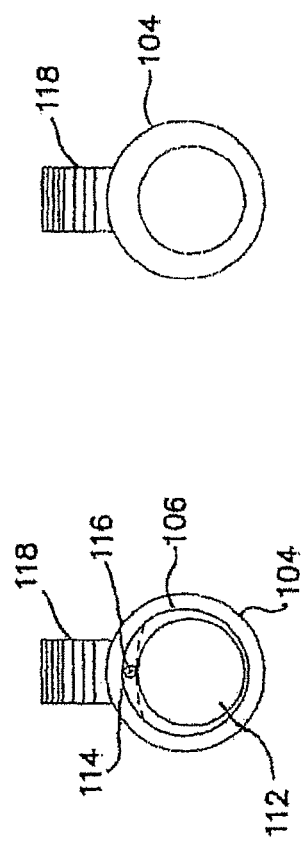

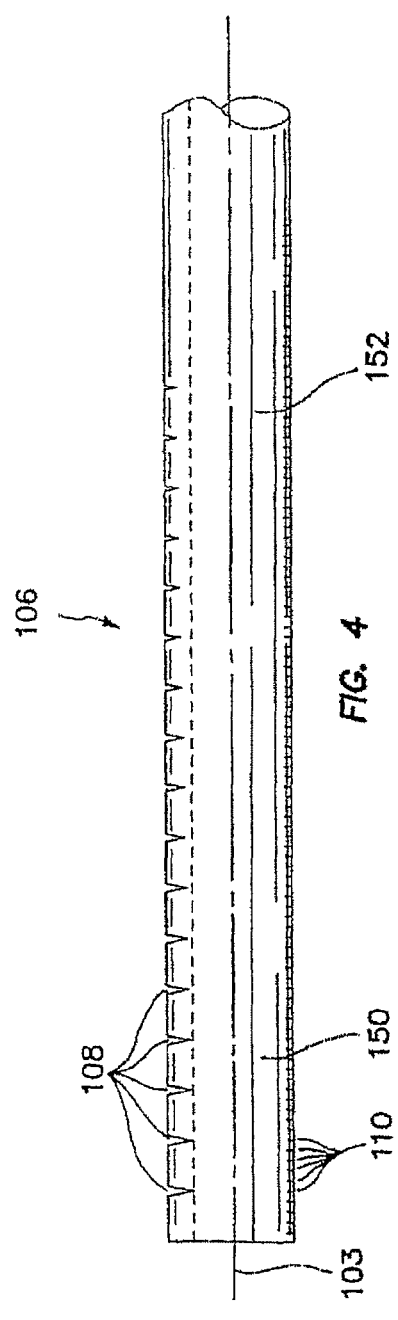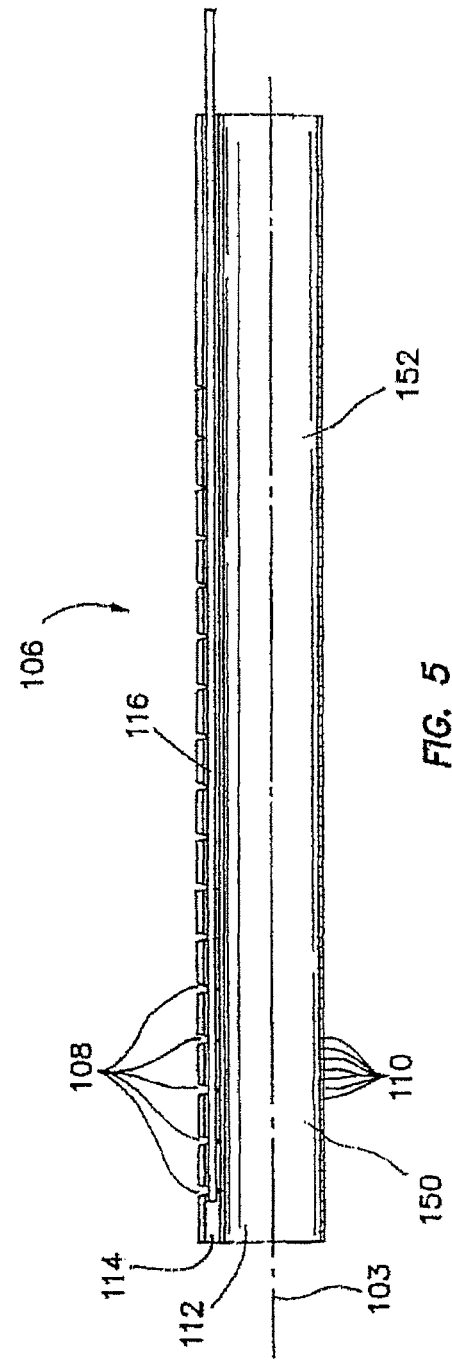

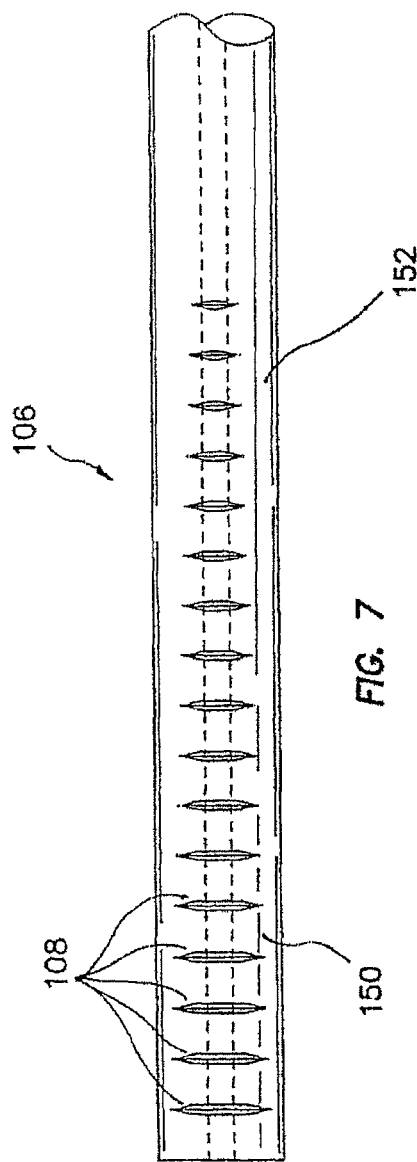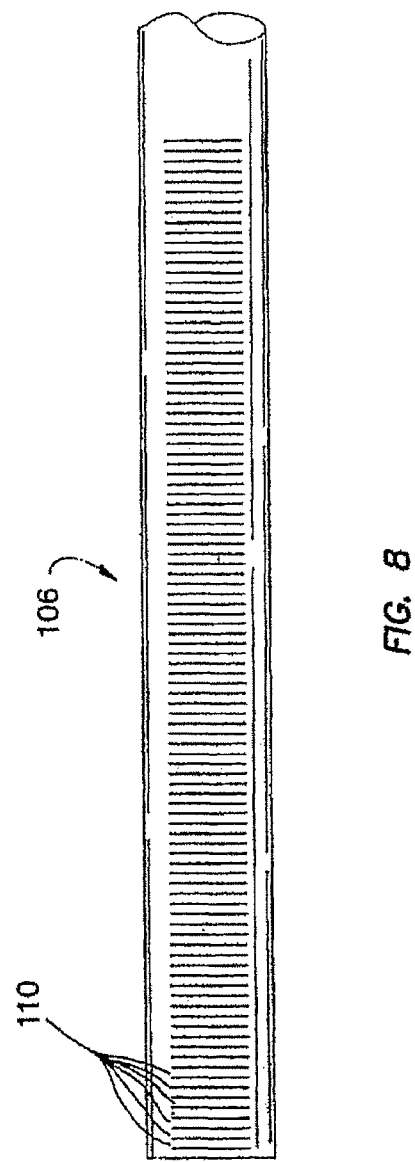

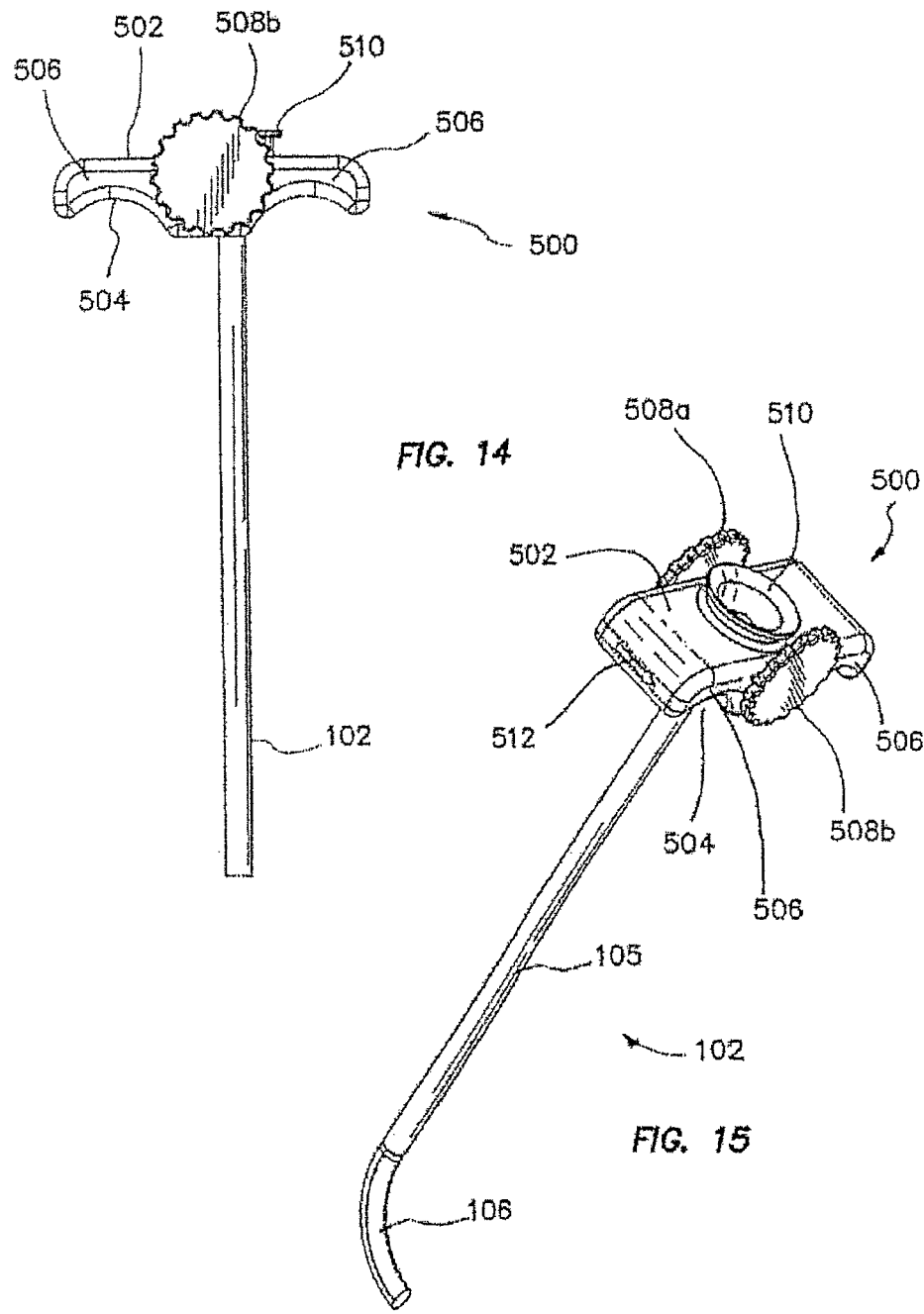

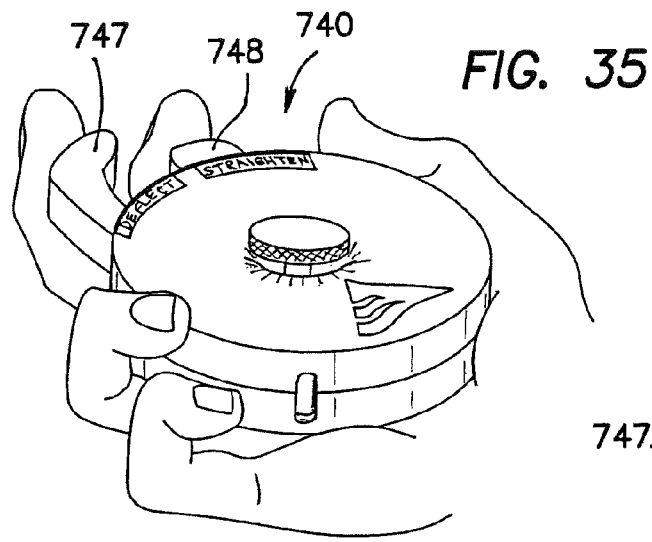
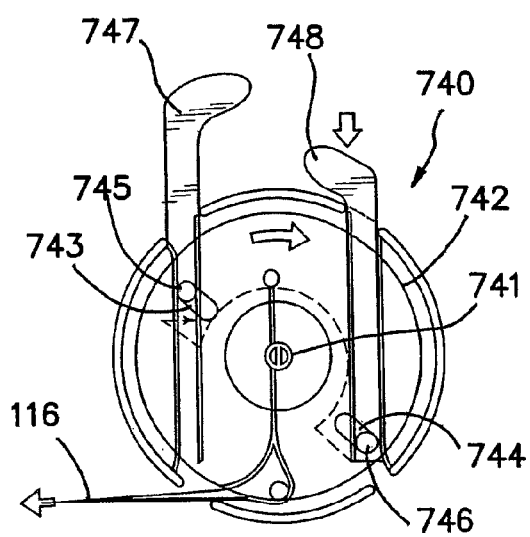
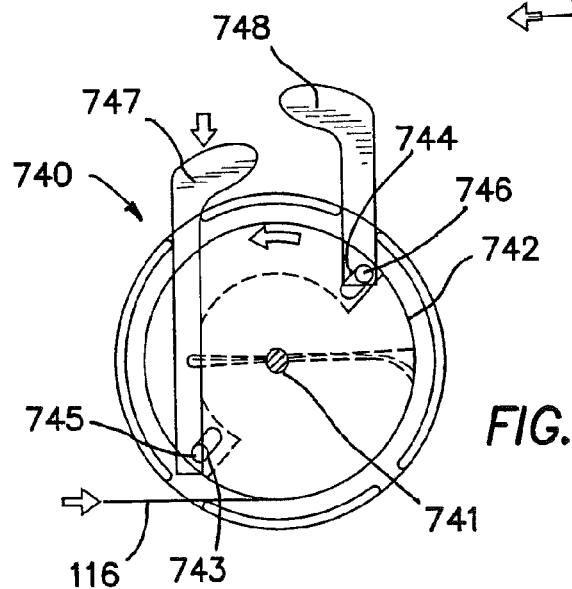
FIG. 35
FIG. 36A
FIG. 36B

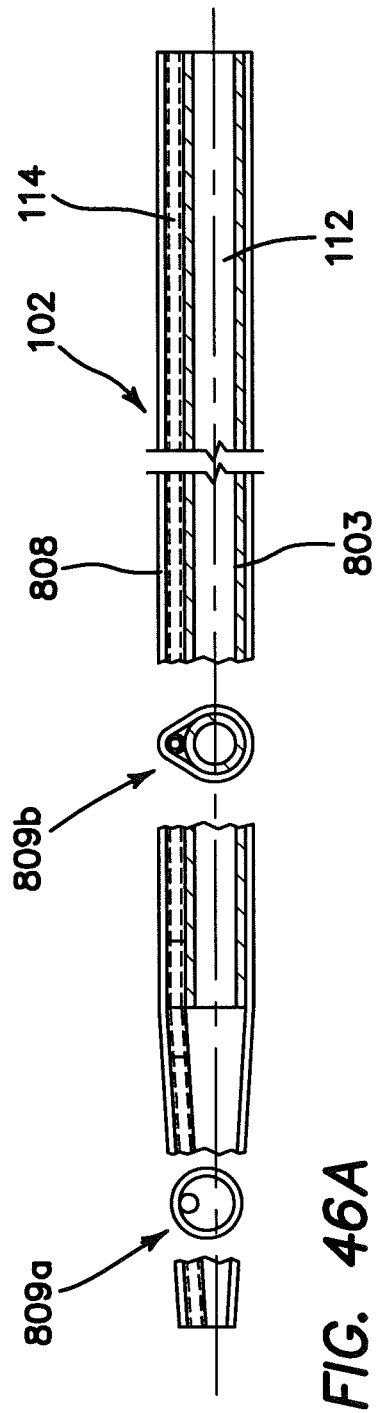

STEERABLE KINK-RESISTANT SHEATH

CROSS-REFERENCE TO RELATED APPLICATIONS

This application is a continuation of U.S. patent application Ser. No. 12/950,782, filed Nov. 19, 2010, which is a continuation of Ser. No. 11/695,449, filed Apr. 2, 2007, now U.S. Pat. No. 7,850,811, which is a divisional of U.S. patent application Ser. No. 10/832,867 filed Apr. 26, 2004, now abandoned, which is a continuation-in-part of U.S. patent application Ser. No. 10/766,138, filed Jan. 28, 2004, now abandoned, and Ser. No. 10/298,116, filed Nov. 15, 2002, now U.S. Pat. No. 7,005,026, and claims benefit of U.S. Provisional Application No. 60/465,310, filed Apr. 25, 2003, the disclosures of which are all hereby incorporated by reference as if set forth in full herein.

BACKGROUND

The present invention generally relates to surgical access devices and, more specifically, to kink resistant sheaths having steerable sections that enable the sheaths to access hard-to-reach body cavities and conduits.

Sheaths and catheters have long been used to access body conduits such as the arterial and venous branches of the vascular system, urinary tract, body cavities such as the thorax and abdomen, and hollow viscous organs such as the stomach, intestines and urinary bladder. More specifically, sheaths and catheters have been used for fluid delivery, fluid recovery, implant delivery and for providing an access pathway for an instrument such as an endoscope. However, many endoscopes, for example, are flexible enough to bend but are not steerable or deflectable in a controlled and/or dynamic manner.

For some instruments, steering has been achieved, for example, by "pre-bending" the distal tip of a surgical device before insertion and then rotating the device once it has been inserted and has reached a branch artery inside the body. If the angle of the bend has to be adjusted, then the device may have to be removed, re-bent and reinserted. This results in greater time spent in the body and thereby increase surgery time. Furthermore, since these sheaths and catheters need to navigate many hard-to-reach areas, it follows that they should be as stiff and yet as flexible as possible. It is also useful that the sheaths and catheters are constructed with thin walls to minimize the diameter of the device and to maximize the radii of the internal lumen.

In trying to balance the flexibility and stiffness issues, manufacturers have attempted to use a variety of materials such as vinyl, polyurethane, silicone, natural rubber, polyester and nylon. A drawback with these plastics is they only work well when the wall is sufficiently thick. That is, when the access sheath is constructed with a thin wall made of a plastic or rubber material, the sheath may bend or twist during use. This may result in potential damage as the sharp edge of the kinked sheath may allow an endoscope or other device to complicate the surgical procedure. Moreover, a bent or kinked sheath is useless because it cannot communicate and it does not allow the passage of an instrument. As such, there is a desire in the art for a steerable access sheath that is durable enough to provide sufficient strength and stiffness to be guided through a body cavity or tissue and, at the same time, be flexible enough to perform intricate manipulations through the body cavity or tissue. In particular, it would be desirable to have a steerable access sheath having a thin wall section, a large lumen, an atraumatic distal end and a kink resistant construction.

SUMMARY

A surgical access device or a steerable kink resistant access device, is provided having an elongate body and a steerable portion. The access sheath has an outside diameter sufficiently small so that it may be inserted into a body cavity or conduit. The steerable portion and the elongate body may have variable stiffness depending on the application of the access sheath. The access sheath typically has two internal lumen, a primary lumen and a secondary lumen. The primary lumen is sized and configured as an access to a surgical site or the target of a surgical procedure, and operates to advance diagnostic and therapeutic elements to the surgical site or target. The secondary lumen is sized and configured to contain a tensioning device such as a control or pull wire that, when acted upon, will deflect the steerable portion. The tensioning device may be made of a kink resistant material such as Nitinol, a braided cable or any flexible strand or wire. The tensioning device extends through the secondary lumen and is attached to a handle portion operatively connected to the proximal end of the access sheath. The handle portion may include a control knob to control the tensioning or loosening of the tensioning device.

In one embodiment of the present invention, a surgical access device is provided comprising an elongated body and an actuator. The elongated body has a proximal end, a distal end, and a steerable region. The body includes a primary lumen and a secondary lumen both extending through the body with the secondary lumen having a tensioning device extending through the secondary lumen and connected to the steerable region of the elongated body. The actuator is connected to the tensioning device distally from the proximal end of the elongated body to control tension of the tensioning device. In one aspect of the present invention, the actuator has a hand-engaging extension, a funnel-shaped entry or entry which is sized and configured to guide an obturator, dilator, ureteroscope and/or other instrumentation into the actuator. The steerable portion may be deflected through the action of the pull wire, which may be connected to an axle in the actuator. That is, as the actuator is manipulated, the pull wire imparts a pulling force on the steerable portion of the sheath, thereby causing the steerable portion to deflect. In another aspect of the invention, passive and/or active directional indicators may be placed on each of the hand-engaging extensions of the hand-piece to indicate the direction of distal deflection or bending of the access sheath.

In one embodiment, a surgical access device comprises a tube having a proximal end, a distal end, a steerable region, and an enlarged entry, the tube including a primary lumen and a secondary lumen both extending through the tube and means for deflecting the steerable portion of the tube. In another aspect of the present invention, a surgical access device comprises a tube having a substantially rigid portion having a first diameter and a substantially flexible portion having a second diameter and extending from the substantially rigid portion, the first diameter being smaller than the second diameter. The tube also includes a primary lumen and a secondary lumen both extending through the tube, the secondary lumen having a pull wire extending through the secondary lumen and connected to the flexible portion of the elongated body. A connector having a distal end connected to the tube and a proximal end including a funnel-shaped portion is also included with the pull wire extending through the connector from the distal end to the proximal end. A plastic tubing is connected to the connector through which the pull wire extends through and a handle is connected to the plastic tubing and including an axle disposed within the handle and a knob connected to and outside the handle, the axle connected to the pull wire and the knob.

In another embodiment, a method of using a surgical access device with a dilator and the access device comprising an elongated body having a proximal end, a distal end, and a steerable region, the body including a primary lumen and a secondary lumen both extending through the body, the secondary lumen having a tensioning device extending through the secondary lumen and connected to the steerable region of the elongated body, and an actuator connected to the tensioning device distally from the proximal end of the elongated body to control tension of the tensioning device is provided. The method comprises inserting the dilator through the primary lumen of the access device, removing the dilator from the access device after the access device is inserted into the patient, and manipulating the actuator to a first position to deflect the steerable region to form an arc.

The access sheath may comprise an extruded multi-lumen plastic tube or a tube molded from a plastic or rubber-like material including polyvinyl chloride, polyester, silicone elastomer, natural or synthetic rubber and polyurethane. The material may range in hardness from around 40 Shore A to 70 Shore D. A structure such as a spring can also be molded into the tube of the access sheath to facilitate kink resistance. More specifically, the access sheath may be formed with an inner plastic body, surrounded by a metal spring coil, which is further covered by an outer plastic body.

In one aspect of the present invention, a method of manufacturing a surgical access device is provided. The method comprises wrapping a first wire around a mandrel, resting a first tube on the first wire, the first tube extending further in length than the first wire along the mandrel, inserting the mandrel through a second tube, and heating the second tube, the mandrel, the first wire and the first tube. In another embodiment, a method of manufacturing a surgical access device comprises assembling a plurality of first ring-shaped members around a mandrel, resting a first tube on the first connecting member, inserting the mandrel through a second tube, and heating the second tube, the mandrel, the first connecting member and the first tube.

In one aspect of steerability of the invention, a tightly wound spring may be placed in the secondary lumen of the access sheath to facilitate movement of the tensioning device inserted therethrough. The spring may be bonded or otherwise fixed to the secondary lumen. Among other features, the spring operates to isolate forces applied by the tensioning device such that only the steerable portion is deflected while the elongate body remains relatively firm when the tensioning device is acted upon. The spring may be coated with a lubricious material further facilitating movement of the tensioning device. The spring may line the entire secondary lumen or portions of the secondary lumen and the spring may be stretched in certain sections to facilitate isolation of the tension force. In another embodiment of the present invention, the tensioning device may be a flattened member extending through at least the steerable portion of the access sheath.

In yet another aspect of the invention, the steerable portion may include a plurality of radially and longitudinally spaced notches and slits disposed on opposite sides of each other facilitating radial deflection of the distal portion in the desired direction or angle. The notches and slits may be of any desired width, length, depth and shape in accordance with the use and flexure requirements of the access sheath. The slits may be narrower and shallower than the notches to provide a "weak-side/strong-side" arrangement of the steerable portion that allows the access sheath to be predisposed to bending in the desired direction.

Many of the attendant features of this invention will be more readily appreciated as the same becomes better understood by reference to the following detailed description and considered in connection with the accompanying drawings in which like reference symbols designate like parts throughout.

BRIEF DESCRIPTION OF THE DRAWINGS

FIG. 1 illustrates a surgical access device or steerable kink resistant access device in accordance with one embodiment of the present invention;

FIG. 2 is a front view of the distal end of the access device of FIG. 1;

FIG. 3 is a rear view of the proximal end of the access device of FIG. 1;

FIG. 4 is an enlarged side view of the distal portion of the access sheath of FIG. 1;

FIG. 5 is a side-section view of the distal portion of the access sheath of FIG. 4;

FIG. 7 is a top view of the distal portion of the access sheath of the present invention;

FIG. 8 is a bottom view of the distal portion of the access sheath of the present invention;

FIG. 14 is a side view of the actuation hand-piece of FIG. 13;

FIG. 15 illustrates a perspective view of an actuation hand-piece of the invention including a directional indicator showing the direction of deflection or bending of the access sheath;

FIG. 35 illustrates a perspective view of an actuation hand-piece in accordance with one embodiment of the present invention;

FIGS. 36A-B illustrate cross-sectional views of the actuation hand-piece of FIG. 35;

FIGS. 43-45 and 46A-C illustrate cross-sectional views of embodiments of an access sheath in various stages of fabrication in accordance with the present invention.

DETAILED DESCRIPTION

Figure 6:
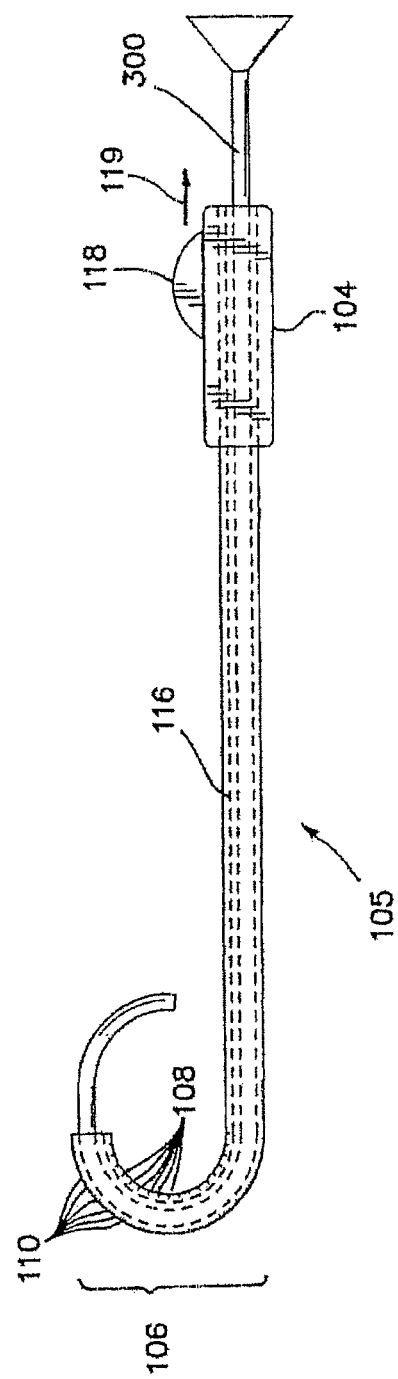
FIG. 6 illustrates a steerable kink resistant access device of the present invention with its distal portion deflected.

FIGS. 1-3 illustrate a surgical access device or steerable kink resistant access device 100 in accordance with the one embodiment of the present invention for use in, among other fields, cardiology, urology, radiology, electrophysiology and gastroenterology. Access device 100 comprises an access sheath 102 having a longitudinal axis 103 extending from a proximal end to a distal end, and a handle portion 104 operatively connected to the proximal end of the access sheath 102. The access sheath 102 includes an elongated body 105 and a steerable region or portion 106. It is appreciated that the steerable portion 106 may be formed anywhere along the access sheath 102. It is further appreciated that the steerable portion 106 and the elongated body 105 may have variable stiffness depending on the application of the access sheath 102. The access sheath 102 has an outside diameter sufficiently small so that it may be inserted into a body cavity or conduit. The access sheath 102 typically has two internal lumen, a primary lumen 112 and a secondary lumen 114, as illustrated in FIG. 2.

The primary lumen 112 is sized and configured as an access to a surgical site or the target of a surgical procedure. In particular, primary lumen 112 operates to advance diagnostic and therapeutic elements to the surgical site or target. The secondary lumen 114 is sized and configured to contain a tensioning device 116 such as a control or pull wire that, when acted upon, will deflect the steerable portion 106 of the access sheath 102. The tensioning device 116 extends through the secondary lumen 114 and is attached to the actuator or handle portion 104 at one end and to a distal portion 107 of the steerable portion 106 at the other end. The handle portion 104 may include a thumb-actuated knob 118 controlling the tensioning device 116. For example, the knob 118 may be drawn proximally in a direction 119 to provide tension to the tensioning device 116 or cause the tensioning device to tense or distally in a direction 120 to loosen tension or cause the tensioning device 116 to loosen.

In another embodiment of the present invention, FIGS. 13-16 illustrate an actuator or actuation hand-piece 500 having a proximally-facing portion 502, a distally-facing portion 504, hand-engaging extensions 506, and at least one thumbwheel member 508a,b. The proximally-facing portion 502 has a generally flat support surface and includes a funnel-shaped entry portion 510. The funnel-shaped entry portion 510 is sized and configured to guide an obturator and other instrumentation into a working channel within the hand-piece 500. The distally-facing portion 504 is connected to the access sheath 102. The working channel of hand-piece 500 is sized and configured to form a transition into the primary lumen 112 of the access sheath 102. The hand-engaging extensions 506 are sized and shaped to accommodate two extended human fingers in a holding position. The at least one thumbwheel 508 allows a user to deflect the steerable portion 106 of the access sheath 102.

The steerable portion 106 may be deflected through the action of a tensioning device 116, such as a pull wire or control wire associated with the secondary lumen 114 within the access sheath 102. The tensioning device 116 may be connected to an axle positioned between two thumbwheels 508a and 508b or at least one thumbwheel and an opposing side of hand-piece 500. As the thumbwheels 508a and 508b are rotated, the tensioning device 116 imparts a pulling force on the steerable portion 106 of sheath 102, thereby causing portion 106 to deflect. In one aspect of the present invention, directional indicators 512 may be placed on each of hand-engaging extensions 506 of hand-piece 500 to indicate the direction of distal deflection or bending of access sheath 102.

It is appreciated that the actuator or actuation hand-piece of the invention may be remotely attached to the associated access sheath to control the tensioning and loosening of the tensioning device. In this case, the hand-piece may be connected to a flexible tubing or body, which is connected to the access sheath. By providing a remote access point or attachment, the thumbwheels of the hand-piece, for example, may be placed away from the surgical site so that they do not prevent or interfere with full insertion of the working length of the access sheath. It is further appreciated that the access sheath may comprise a plurality of pull wires attached to a plurality of thumbwheels of an actuation hand-piece to deflect the steerable portion of the sheath in different directions.

Figure 17:
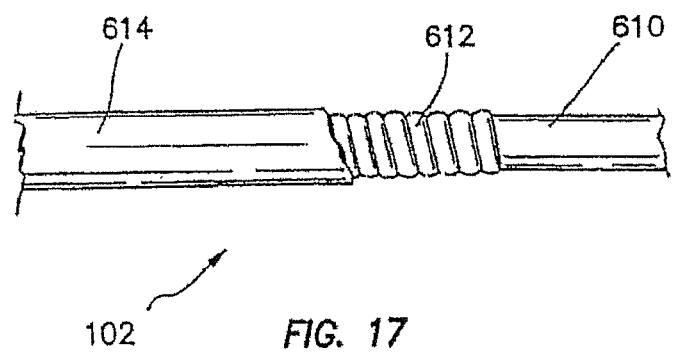
FIG. 17 illustrates a side-elevation view illustrating a spring embodiment of the tube associated with the sheath of the present invention.

In one embodiment of the invention, the access sheath 102 comprises an extruded multi-lumen plastic tube. Alternatively, the access sheath 102 may be molded from a plastic or rubber-like material. Preferred materials include polyvinyl chloride, polyester, silicone elastomer, natural or synthetic rubber, polyurethane or the like. The materials may range in hardness from around 40 Shore A to 70 Shore D. These materials are generally flexible and durable. In another embodiment of the invention as illustrated in FIG. 17, a structure such as a spring can be molded into the tube of the sheath to facilitate kink resistance. More specifically, the access sheath 102 may be formed with an inner plastic body 610, surrounded by a metal spring coil 612, which is further covered by an outer body 614. This particular embodiment of access sheath 102 provides a high degree of kink resistance. The inner body 610 provides a smooth surface within the sheath, which facilitates passage of instrumentation. The spring coil 612 adds kink resistance to the sheath tube, while the outer body 614 provides a suitable covering for the coils of the spring 612.

In one aspect of steerability of the present invention, a tightly wound spring may be placed in the secondary lumen 114 of the access sheath 102 to facilitate movement of the tensioning device 116 inserted there through. The spring may be bonded or otherwise fixed to the secondary lumen 114. Among other features, the spring operates to isolate forces applied by the tensioning device 116, which is inserted through the spring and is attached to the distal portion 107 of the steerable portion 106. In particular, the spring adds stability and rigidity to the elongate body 105 when the tensioning device 116 is acted upon such that only the steerable portion 106 is bent or steered. Furthermore, the spring operates to direct the tension force applied on the device 116 to the steerable portion 106 so as to allow deflection of only the portion 106 and not the elongate body 105. That is, the tension force is isolated to the steerable portion 106, which may be formed anywhere along the access sheath 102. The spring may be coated with a lubricious material further facilitating movement of the tensioning device 116. The spring may line or cover the inner surface area of the entire secondary lumen 114 or just portions of the secondary lumen 114 to facilitate isolation of the tension force.

The spring may be constructed from a 0.005-inch diameter wire that is tightly wound forming a closed wound spring having a 0.02-inch outer diameter. The distal 0.5 to 2 inches of the spring may be stretched to an open wound state such that the windings have an approximately 0.02-inch gap between them. This stretched portion of the spring facilitates isolation of the tension force applied by the tensioning device 116. The spring may be coated, for example, in a plastic jacket and bonded to the secondary lumen 114 from the proximal end of the spring to the proximal end of the stretched portion. The stretched portion is then left free to move and/or compress in the plastic jacket. The distal end of the stretched portion may be anchored to the distal end of the access sheath 102 along with the tensioning device 116. The distal end of the plastic jacket may also be bonded to the distal end of the access sheath 102 along with the tensioning device 116 and the spring although these elements do not require a common bonding point or bonding method.

As discussed above, the proximal end of the access sheath 102 may be directly or remotely attached to handle portion 104 or actuator or hand-piece 500, which allows the operator to place tension on the tensioning device 116, such as a control or pull wire, while maintaining the position of the catheter. This tension causes the stretched portion of the 0.02-inch diameter spring to collapse and this, in turn, forces the sheath to bend in the region where the stretched portion of the spring is located. It is appreciated that the stretched portion may be formed anywhere along the catheter or surgical access device that may require bending, and is not limited to the distal end of the device. In addition, more than one deflection assembly of spring and tensioning device may be added to the access device to create deflection in different regions or planes. The amount of bending or deflection will in some way be proportional to the amount of force or tension placed on the tensioning device.

Figure 12:
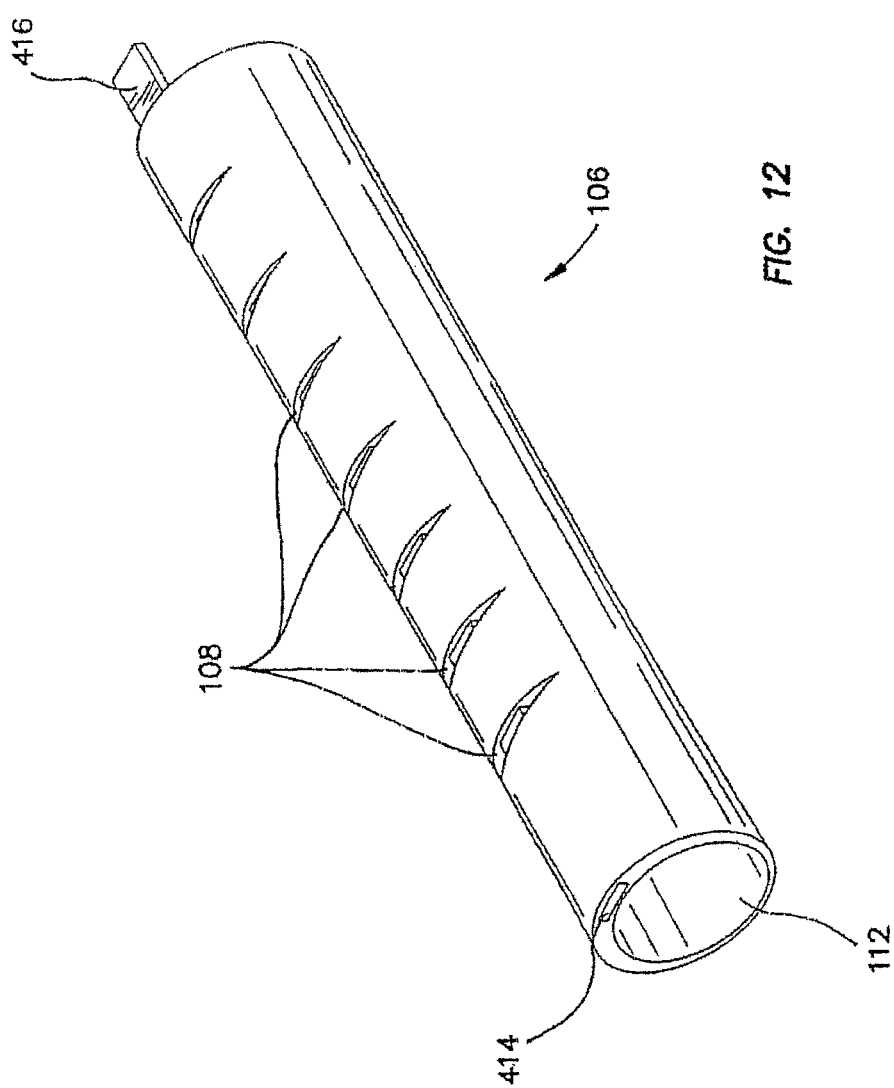
FIG. 12 illustrates a perspective view of the distal portion of an access sheath having a flattened tensioning member.
Figure 13:
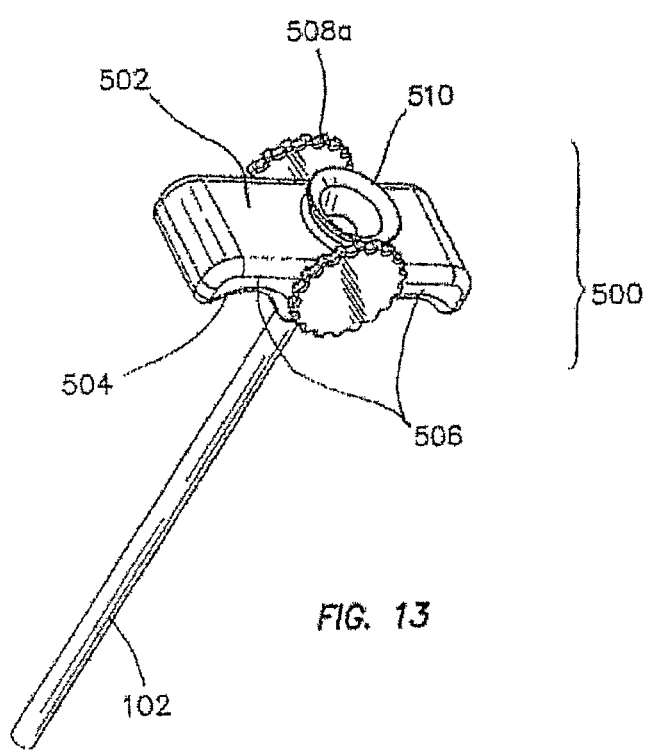
FIG. 13 illustrates a perspective view of an actuator or actuation hand-piece in accordance with another embodiment of the present invention.
Figure 16:
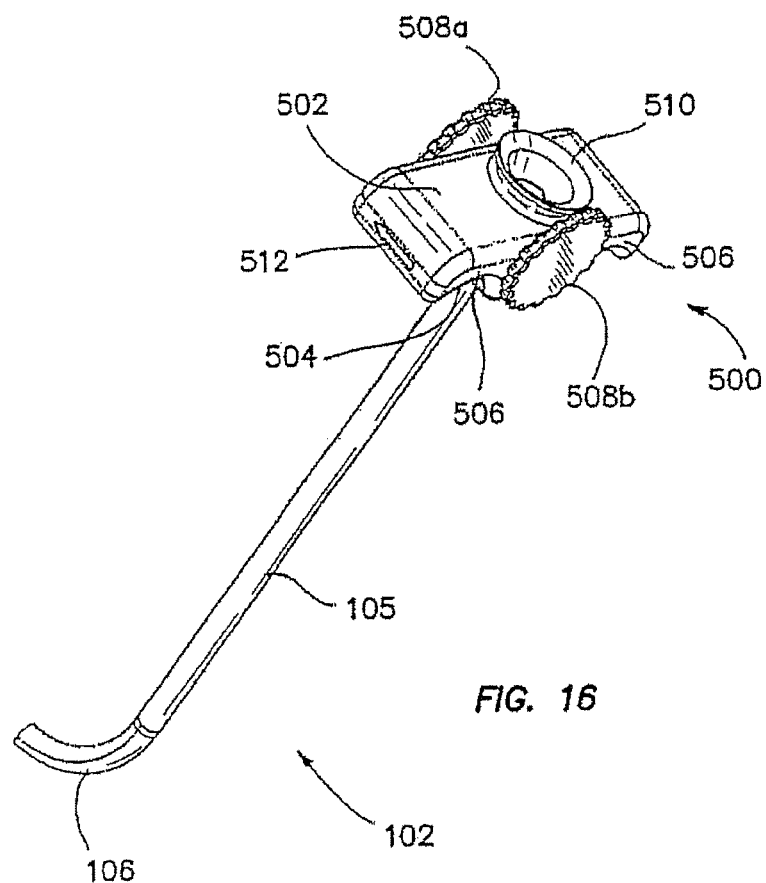
FIG. 16 illustrates another perspective view of an actuation hand-piece of the invention including a directional indicator.

The tensioning device 116 is, in one embodiment, a control or pull wire made of Nitinol, a braided cable or any flexible strand or wire. In one embodiment, the control wire is inserted through the spring such that it runs through the secondary lumen 114 as illustrated in FIG. 5. The proximal end of the tensioning device 116, e.g., a control or pull wire, is connected to an actuator such as the knob 118 of the handle portion 104. The distal end of the control or pull wire, as previously described, is attached to the distal portion 107 of steerable portion 106. In another aspect of the invention as illustrated in FIG. 12, the tensioning device 416 may be a flattened or flat member extending through at least the steerable portion 106 of the access sheath 102.

In another aspect of the present invention as illustrated in FIGS. 1 and 4-5, the steerable portion 106 includes a plurality of radially and longitudinally spaced notches 108 and slits 110 disposed on opposite sides of each other facilitating radial deflection of the distal portion 107 in a desired direction or angle. The notches 108 and slits 110 are cut into the access sheath 102 across the longitudinal axis 103. The degree of deflection may vary greatly based on many factors such as the number, size, direction, shape and spacing of the notches 108 and slits 110. The notches 108 are cut deeper and wider at a distal end 150 than they are at a proximal end 152 of steerable portion 106. The slits 110 comprise of very shallow cuts to provide a reduction in resistance to stretching as the steerable portion 106 is bent or deflected toward the notches 108.

As discussed above, the notches 108 and slits 110 may be of any desired width, length, depth and shape. The number of notches 108 and slits 110 in the steerable portion 106 can be varied in accordance with the use and flexure requirements of the access sheath 102. However, in one embodiment, the slits 110 are narrower and shallower than the notches 108 to provide a "weak-side/strong-side" arrangement of the steerable portion 106 so as to allow the access sheath 102 to be predisposed to bending in the desired direction. That is, when the control wire of the tensioning device 116 is drawn proximally as illustrated in FIG. 6, the more flexible side of the steerable portion 106, i.e., the side with notches 108, will give first thereby bending in the direction of the notches. Moreover, the distal end 150 of the steerable portion 106 with the deeper and wider notches 108 will bend first as the bending progressively moves toward the proximal end 152 having shallower and narrower notches. It is appreciated that the notches 108 may extend through the wall of the access sheath 102.

Referring now to FIGS. 7 and 8, the opposing series of notches 108 and slits 110 are further illustrated. The notches 108, as discussed above, provide a "weak-side" or preferred bend path as the notches 108 are closed when bent. It can be seen that the notches 108 are wedge-shaped and have material removed from them. There is, therefore, sufficient room for the material adjacent to each notch to approximate, thereby shortening the length of the steerable portion 106 on the weak-side. In contrast, the slits 110 are shallow radial cuts made directly opposite the notches 108 with little or no material removed. The slits 110 provide the mechanical equivalent of increased plastic elasticity. That is, the slits 110 allow the material of the steerable portion 106 to stretch beyond the intrinsic properties of the material itself. As a result of this construction, the primary lumen 112 of the steerable portion 106 will not collapse when deformed or bent into a tight circular profile as can be seen in FIG. 6. In other words, the slits 110 will only open to provide an elongation of the "strong-side" and will not collapse to provide a shortening of the "strong-side". The material on either side of the notches 108 and slits 110 maintains the general elongate dimension and forms a continuum of the access sheath 102.

Figure 9:
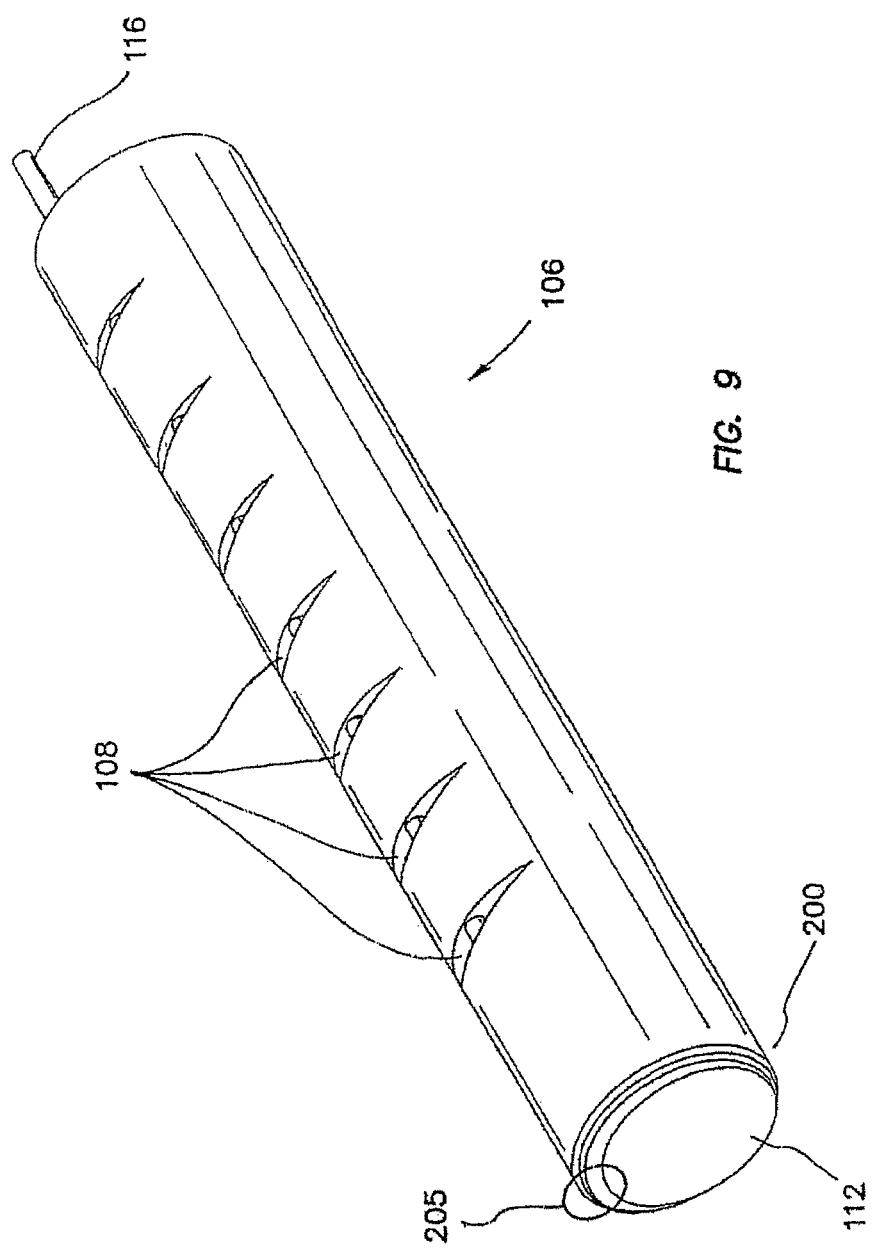
FIG. 9 illustrates the atraumatic distal end of the access sheath of the present invention.
Figure 10:
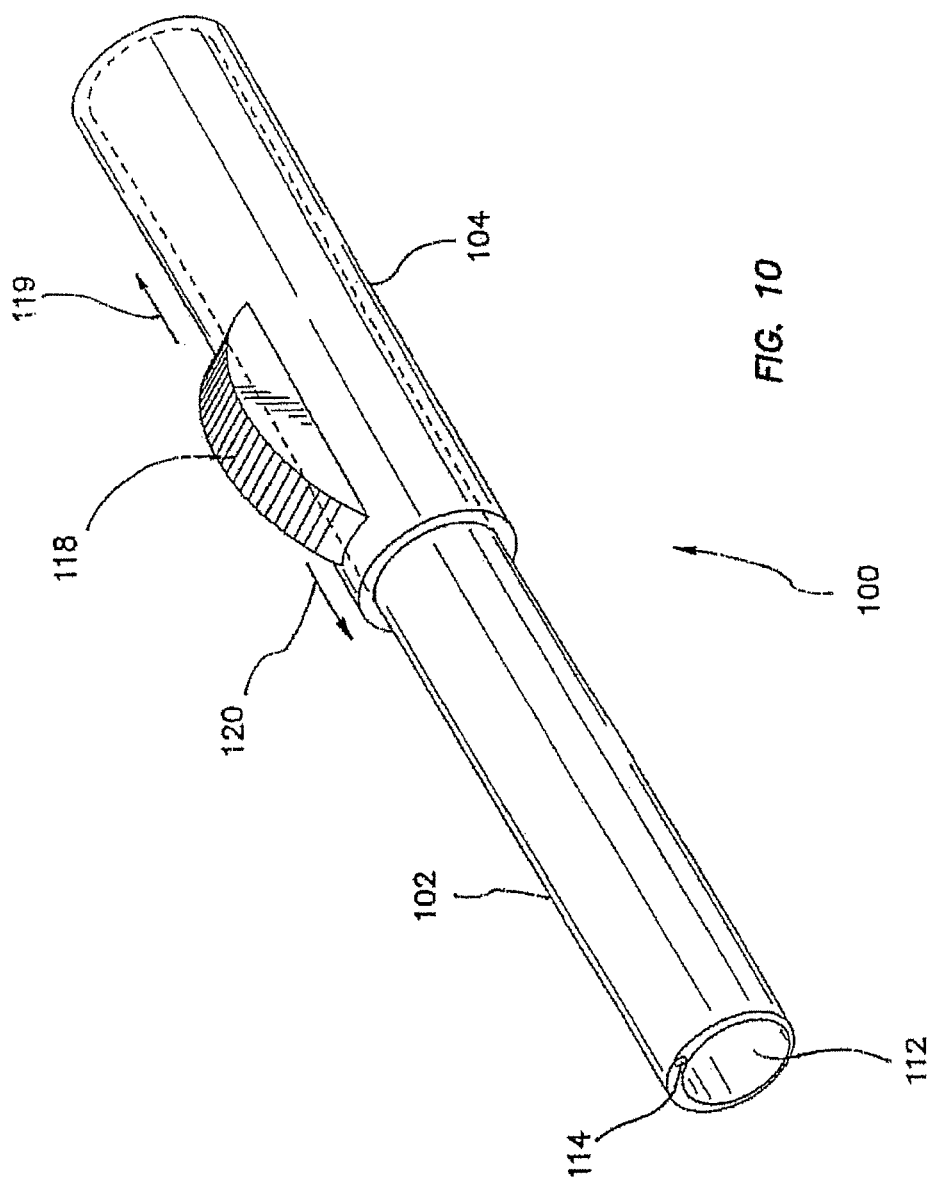
FIG. 10 illustrates an actuator of the access device of the present invention used to control the steerable region or portion of the access sheath.
Figure 11:
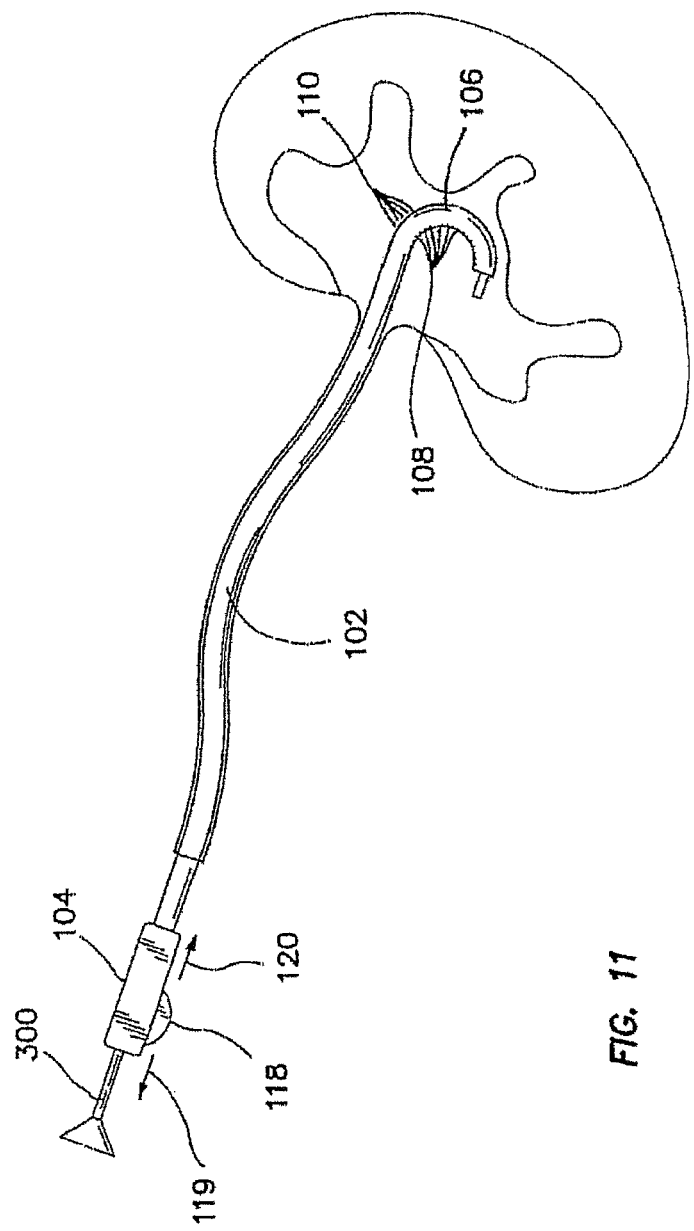
FIG. 11 illustrates the access device of the present invention guiding a scope into a kidney pole.

In another embodiment of the invention as illustrated in FIG. 9, the distal end 200 of the steerable portion 106 has a generally rounded off wall section 205 providing an atraumatic insertion tip. With the current construction of the access sheath having a steerable distal portion, less pushing force is required to advance the access sheath since it may be deflected around, under or over anomalies and irregularities in a body cavity or conduit rather than being forced through the tortuous paths. Surgical instruments such as an ureteroscope 300 may be directed through a steerable access sheath as illustrated in FIGS. 6 and 11. For instance, the steerable access sheath may be used to pass the ureteroscope 300 into the upper and lower poles of the renal calices as generally illustrated in FIG. 11. It is appreciated that flexible ureteroscopes and other flexible endoluminal scopes, including completely passive scopes, may be accurately positioned with the assistance of the steerable access sheaths of the present invention.

Figure 18A:
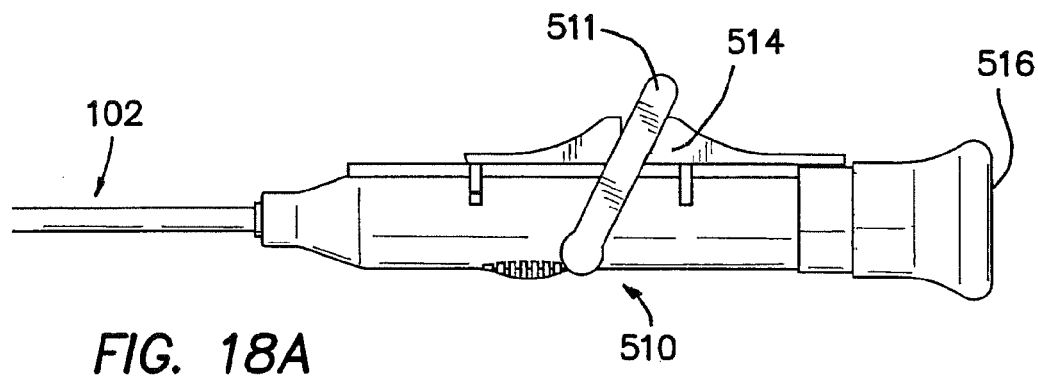
FIG. 18A illustrates a side view of an actuation hand-piece in accordance with one embodiment of the present invention.
Figure 18B:
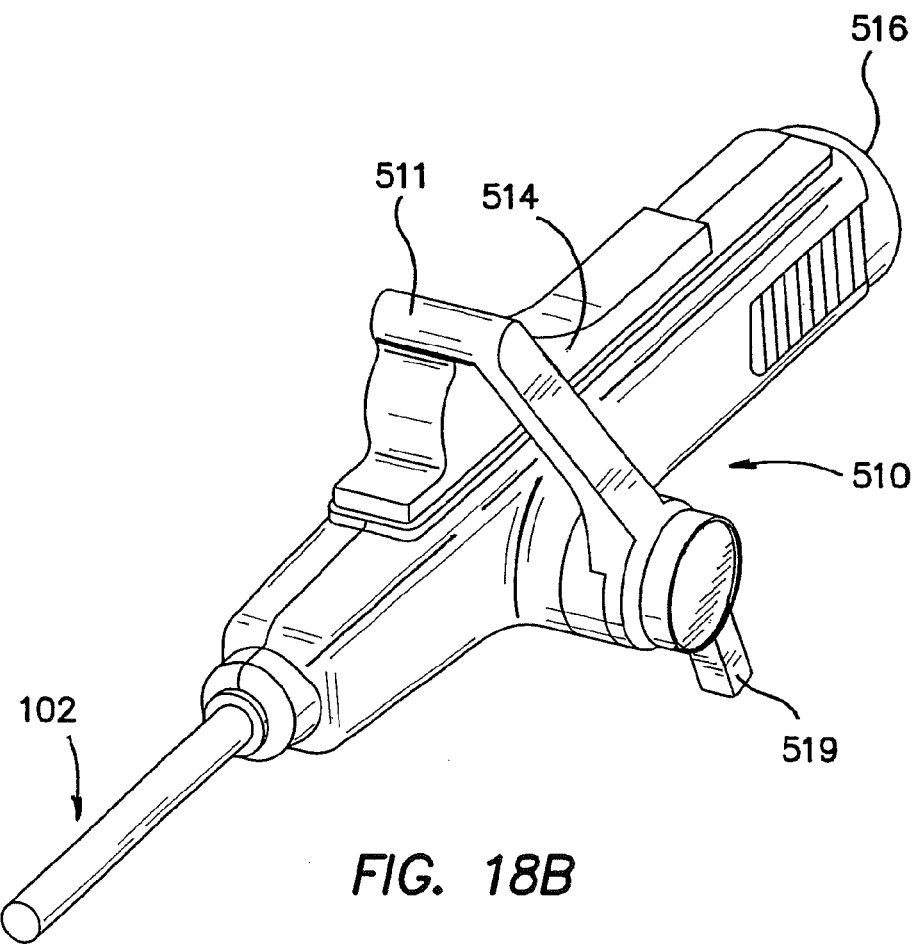
FIG. 18B illustrates a perspective view of an actuation hand-piece in accordance with one embodiment of the present invention.
Figure 19:
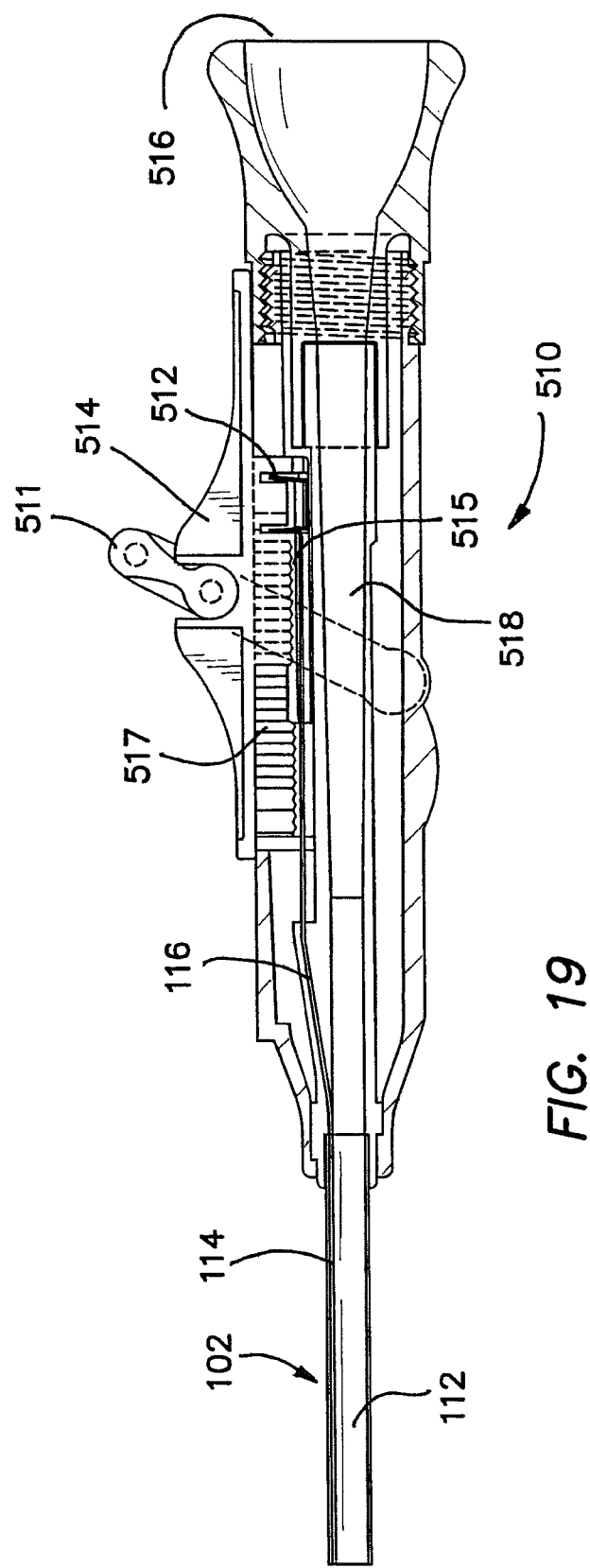
FIG. 19 illustrates a cross-sectional view of the actuation hand-piece of FIGS. 18A-B.

In another embodiment of the present invention, FIGS. 18-19 illustrate an actuation hand-piece or actuator 510 in line with the access sheath 102. The proximal end of the actuator 510 includes a funnel-shaped entry portion 516 that is sized and configured to guide an obturator, dilator, ureteroscope and other instrumentation into a working channel 518 within the actuator 510. The working channel 518 of actuator 510 is sized and configured to form a transition into the primary lumen 112 of the access sheath 102.

The tensioning device 116 extending through the secondary lumen 114 is attached to a bracket 512. A proximal end of the tensioning device 116 is balled, crimped, or otherwise sized or deformed to secure the tensioning device 116 to the bracket 512. The bracket 512 is further connected to a slider 514. A lever 511 connected to the slider 514 allows a user to move the slider 514 and thereby control tensioning device 116. In FIG. 18B, the hand-piece 510 includes a pivotable lever 519 connected to lever 511. Pivotable lever 519 provides a counter actuation point relative to lever 511. In other words, as the lever 519 is moved distally, lever 511 moves proximally and vice versa.

When the slider 514 is moved proximally, the tensioning device 116 imparts a pulling force on the steerable portion 106 (FIG. 1) of access sheath 102 thereby deflecting the steerable portion 106. The slider 514 also includes a plurality of teeth 515 that operatively engage corresponding teeth 517 along the inside of the hand-piece 510. Therefore, as the slider 514 is moved proximally and distally, this engagement allows incremental control of the deflection and straightening of the steerable region or portion 106 of the access sheath 102.

Figure 20:
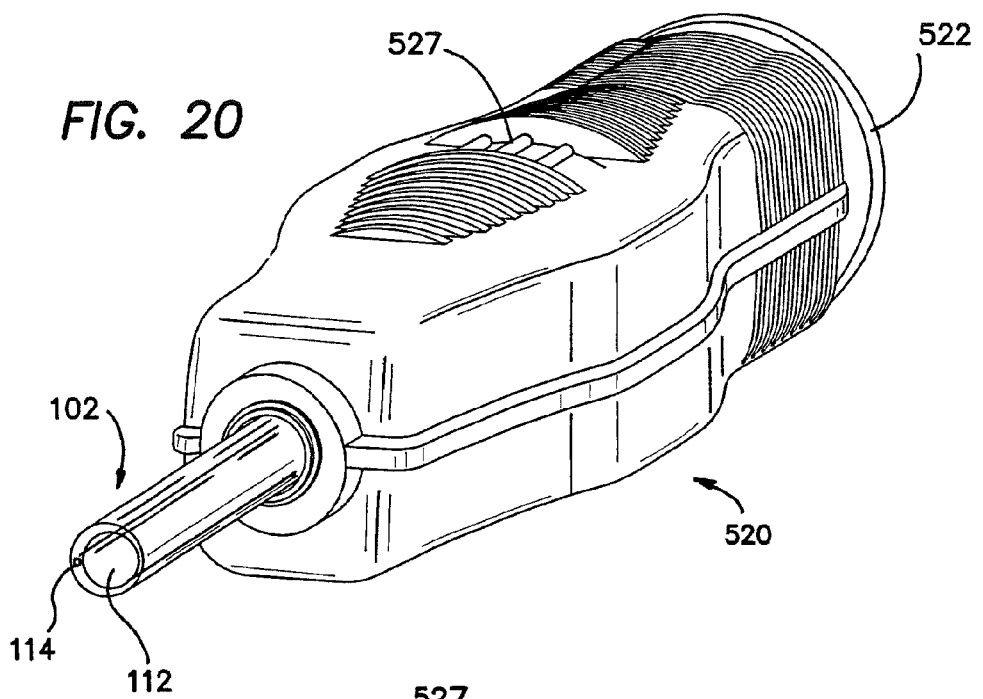
FIG. 20 illustrates a perspective view of an actuation hand-piece in accordance with one embodiment of the invention.
Figure 21A:
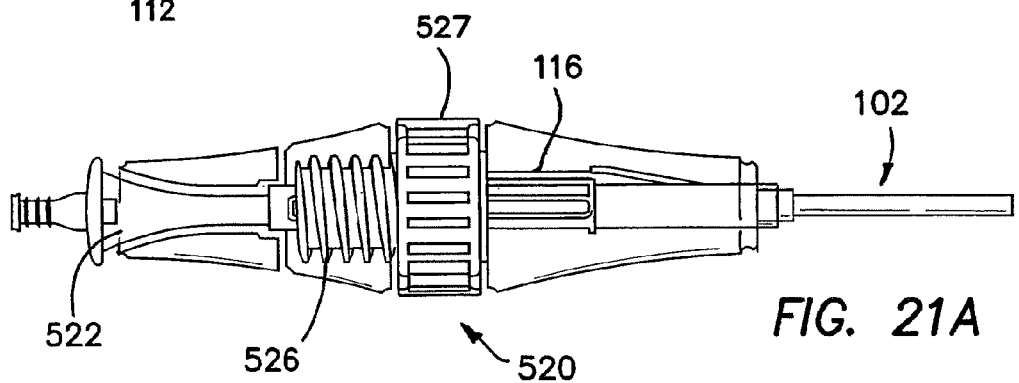
FIG. 21A illustrates a top view of a disassembled actuation hand-piece of FIG. 20.
Figure 21B:
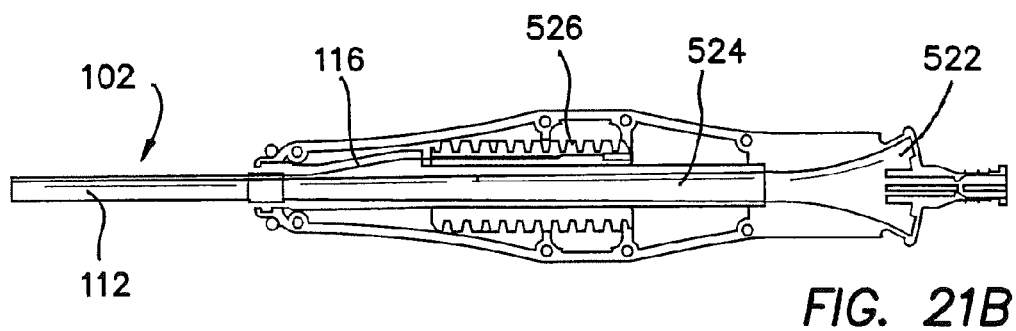
FIG. 21B illustrates a cross-sectional view of the actuation hand-piece of FIG. 20.

Referring now to FIGS. 20-21, an embodiment of an actuator or actuation hand-piece 520 also adapted to be in line with the access sheath 102 is shown. The proximal end of the hand-piece 520 includes a funnel-shaped entry portion 522 connected within the hand-piece 520 to access a working channel 524 which forms a transition into the primary lumen 112 of the access sheath 102.

Tensioning device 116 extending through the secondary lumen 114 is attached to a threaded cylinder 526. A knob 527 surrounding the cylinder 526 is correspondingly threaded to engage the cylinder 526, which allows a user with a twist or turn of the knob 527 in one direction, e.g., clockwise, to move the cylinder 526 linearly, e.g., proximally. As a result, tensioning device 116 also traverses towards the proximal end of the hand-piece 520 to impart a pulling force on the steerable portion 106 thereby deflecting the steerable portion 106 of the access sheath 102. The knob 527 is also allowed to move in the opposite direction moving the threaded cylinder 526 distally to straighten the steerable portion 106 of the access sheath 102. Therefore, the hand-piece 520 provides a rotary or scroll type control of the deflection and/or straightening of the steerable portion 106 of the access sheath 102.

Figure 22:
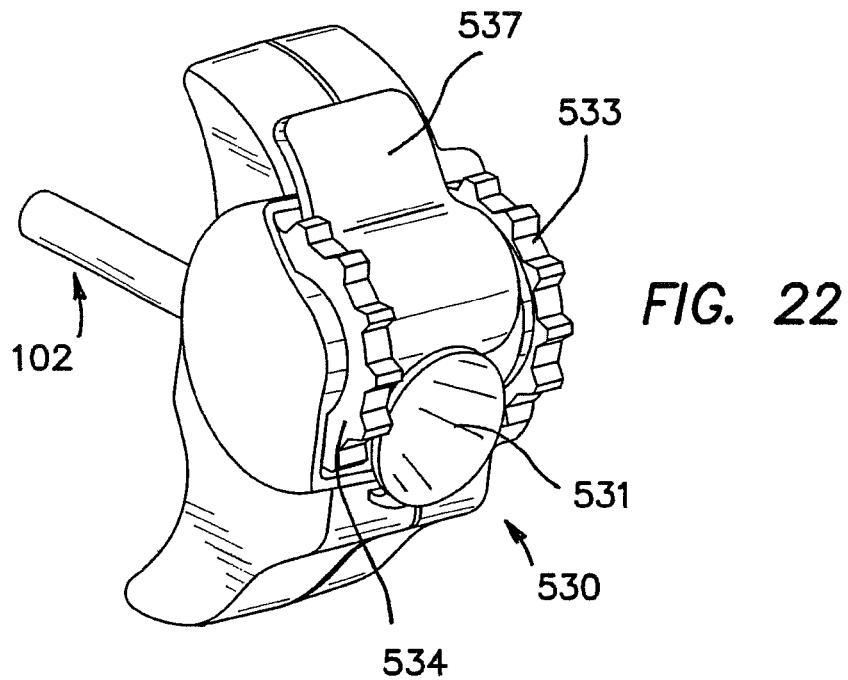
FIG. 22 illustrates a perspective view of an actuation hand-piece in accordance with one embodiment of the invention.
Figure 23A:
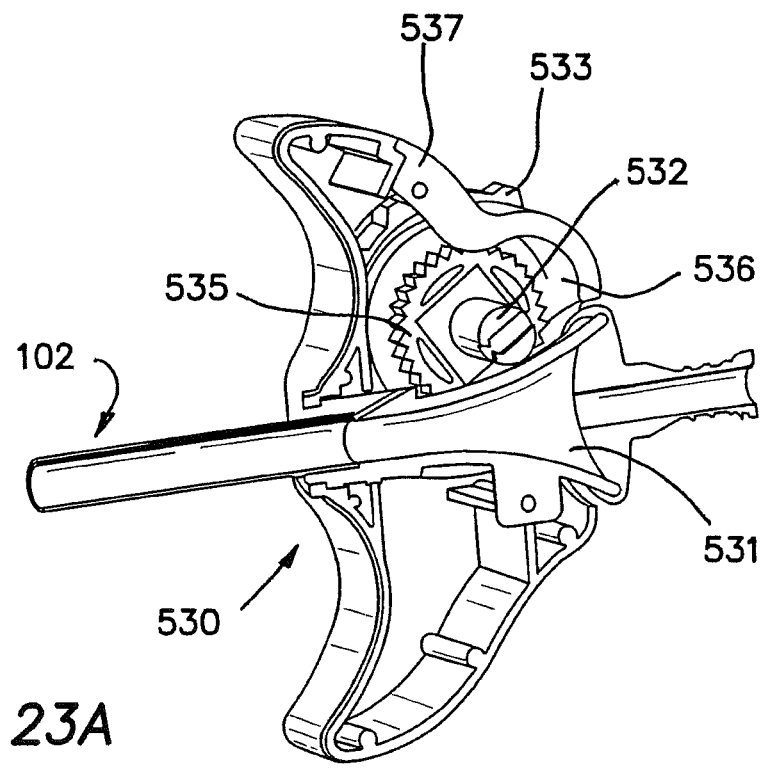
FIG. 23A illustrates a cross-sectional view of the actuation hand-piece of FIG. 22.
Figure 23B:
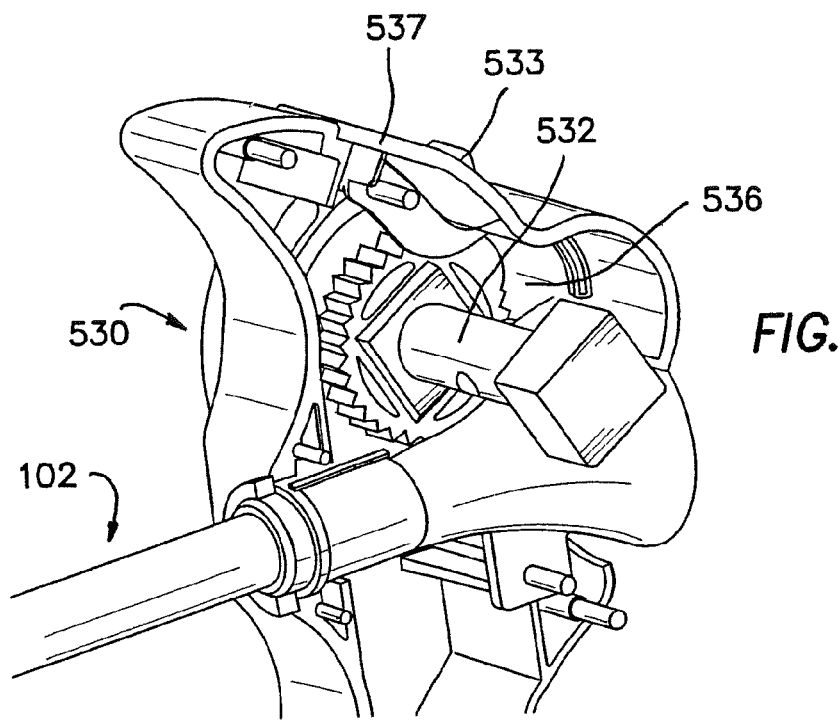
FIG. 23B illustrates a perspective view of a disassembled actuation hand-piece of FIG. 22.
Figure 24:
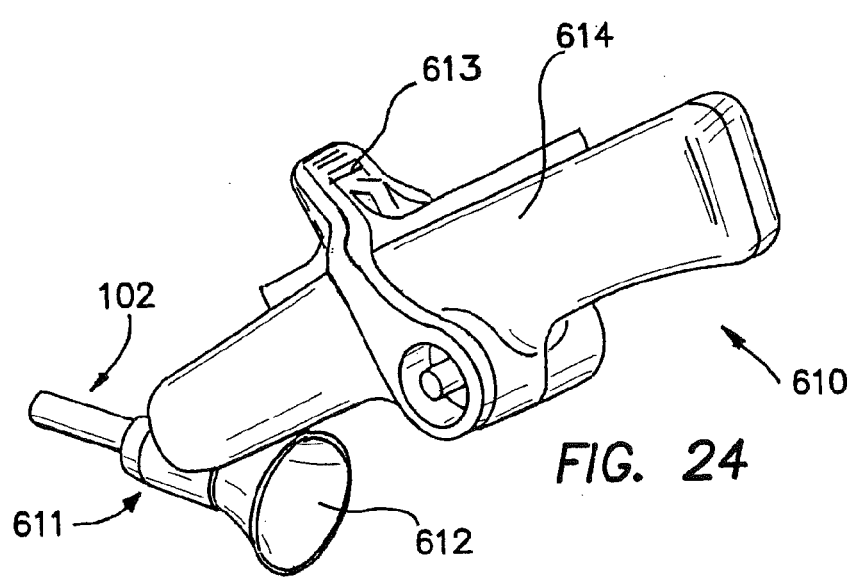
FIG. 24 illustrates a perspective view of an actuator or actuation hand-piece in accordance with one embodiment of the invention.

In another embodiment of the present invention, FIGS. 22-24 illustrate an actuator or actuation hand-piece 530 in line with the access sheath 102, with the hand-piece 530 including a funnel-shaped entry portion 531. An axle 532 disposed within the hand-piece 530 is connected to a tensioning device from the access sheath 102 and connected to two thumb-actuated dials or wheels 533 and 534. In one embodiment, the wheels 533 and 534 are partially disposed within the hand-piece 530. The wheel 533 and/or wheel 534 control the tensioning device. For example, the wheel 533 turned clockwise causes the tensioning device to be drawn proximally to provide tension to the tensioning device, e.g., one or more a pull or control wires. The control wire(s) being drawn proximally wraps or winds around the axle 532 in the hand-piece 530.

The wheels 533 and 534 also include ratchet wheels or a number of radially extending teeth 535 connected to or integrated with the wheels 533 and 534. The teeth 535 operatively engage with a corresponding lever or pawl 536 connected to a trigger 537. The pawl 536 engaged with the teeth 535 permits rotational movement of the wheels 533 and 534 in one direction, e.g., a clockwise direction, while preventing rotational movement in the opposite direction. As such, as the wheels 533 and 534 are turned clockwise, incremental control of the deflection of the steerable portion 106 of the access sheath 102 is provided as the axle 532 in the hand-piece 530 draws the tensioning device 116 proximally. The trigger 537, when actuated, pivots pawl 536 causing pawl 536 to disengage from teeth 535. As a result, the control wire(s) unwind or move distally from the axle 532 whereby the steerable portion 106 of the access sheath 102 straightens.

Figure 25:
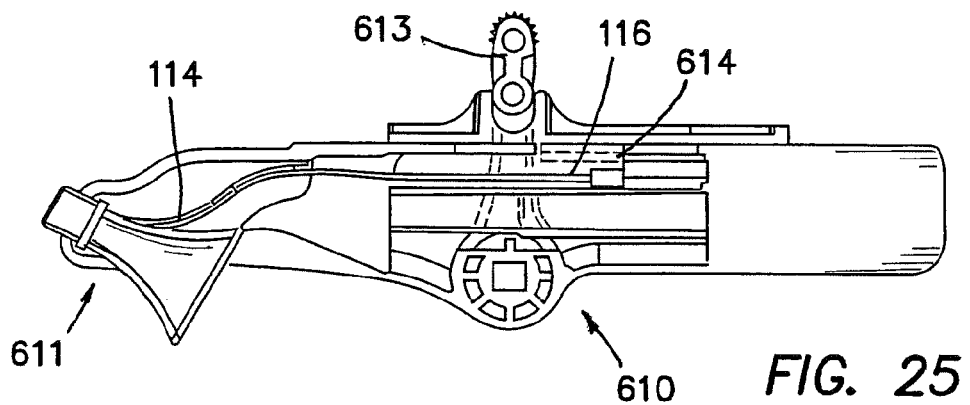
FIG. 25 illustrates a cross-sectional view of the actuation hand-piece of FIG. 24.

Referring now to FIGS. 24-25, an actuator or actuation hand-piece 610 being connected yet offset from the access sheath 102 is shown. As such, the offset hand-piece may reduce the working length used in the access sheath or added to the access sheath with the hand-piece being in line with the access sheath. Additionally, the user may operate the hand-piece proximate to the access sheath to provide a tactile or visual feedback or reminder of the steerable portion 106 of the access sheath 102. The hand-piece 610, in one embodiment, includes or is connected to a connector 611 with a funnel-shaped entry portion 612 that is sized and configured to receive and guide instruments into/out of the access sheath 102. The secondary lumen 114 is separately connected to the hand-piece 610. Through connector 611, in one aspect of the present invention, a conduit connects the secondary lumen 114 and tensioning device 116 to the hand-piece 610.

The tensioning device 116 extending through the secondary lumen 114 is attached to slider 614. A lever 613 connected to the slider 614 allows a user to move the slider 614 that imparts a pulling force on the steerable portion 106 to deflect the steerable portion 106 or a reduction in tension on the steerable portion 106 allowing the steerable portion 106 of the access sheath 102 to straighten. The slider 614, in one aspect of the present invention, includes a plurality of teeth that operatively engage corresponding teeth along the inside of hand-piece 610 to provide incremental control of the deflection and/or straightening of the steerable portion 106 of the access sheath 102.

Figure 26:
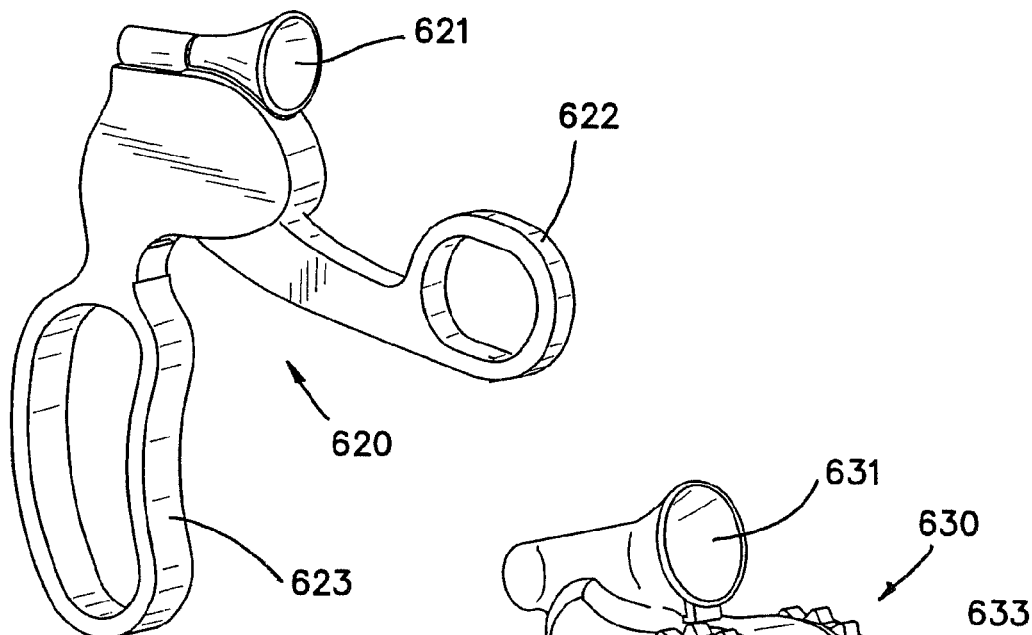
FIG. 26 illustrates a perspective view of an actuation hand-piece in accordance with one embodiment of the present invention.

FIG. 26 illustrates another embodiment of the present invention of an actuator or actuation hand-piece 620 offset from the access sheath 102. The hand-piece 620 includes a funnel-shaped entry portion 621 providing access to the primary lumen of the access sheath 102. The secondary lumen and the tensioning device of the access sheath 102 are also connected to the hand-piece 620. The tensioning device 116, for example, is attached to a movable handle member 622 that is pivotally connected to a stationary handle member 623. In one embodiment, the tensioning device is connected to a semi-circular plate or disc that rotates or pivots as the movable handle member is actuated. Manipulation of the movable handle member 622 allows a user to pull or release the tensioning device 116 to respectively deflect or straighten the steerable portion 106 of the access sheath 102. In one aspect of the present invention, a ratchet mechanism disposed within the hand-piece 620 or between the movable handle member 622 and the stationary handle member 623 is included to provide incremental control of the tensioning device 116 and thus the deflection of the steerable portion 106 of the access sheath 102.

Figure 27:
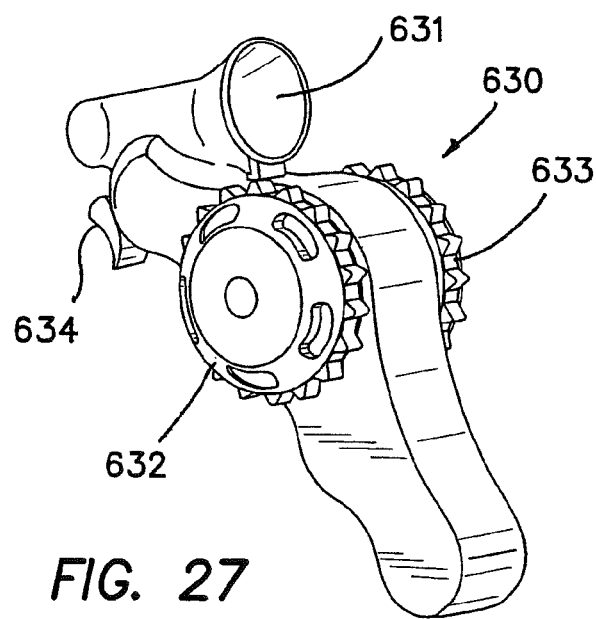
FIG. 27 illustrates a perspective view of an actuation hand-piece in accordance with one embodiment of the present invention.
Figure 28A:
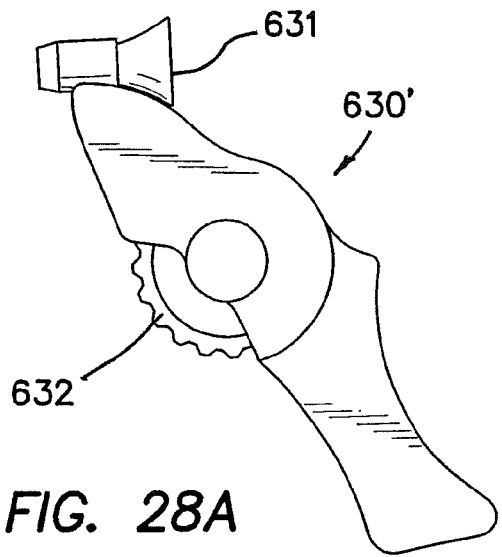
FIG. 28A illustrates a side view of an actuator or actuation hand-piece in accordance with one embodiment of the invention.
Figure 28B:
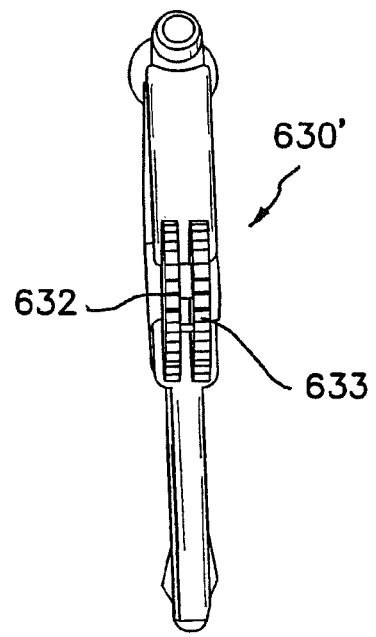
FIG. 28B illustrates another side view of the actuation hand-piece of FIG. 28A.

Referring now to FIGS. 27-28 illustrate an actuator or actuation hand-piece 630 and 630' situated offset from the access sheath 102. The actuation hand-piece 630 and 630' includes a funnel-shaped entry portion 631 and is connected to a tensioning device attached to an axle disposed within the hand-piece 630 and 630'. The axle is connected to two thumb-actuated knobs or wheels 632 and 633. As shown in FIGS. 28A-B, the wheels 632 and 633 are partially disposed within the hand-piece 630'. The wheels 632 and 633 control the tensioning device 116. For example, the wheel 632 and/or wheel 633 may be rotated to provide tension to the tensioning device 116, e.g., a control wire, or to loosen tension in the control wire. In one embodiment, the wheel 632 and 633 are connected to separate and independent control wires adapted to deflect the access sheath in an opposing manner and/or to deflect different portions of the access sheath.

In one aspect of the present invention, a trigger 634, when actuated, locks the wheel 632 and/or wheel 633 thus preventing further movement of the tensioning device 116 and the deflection/straightening of the steerable portion 106 of the access sheath 102. Alternatively, the trigger 634 releases or disengages control of the tensioning device 116 from wheels 632 or 633 to allow the tensioning device to return to its original position.

Figure 29:
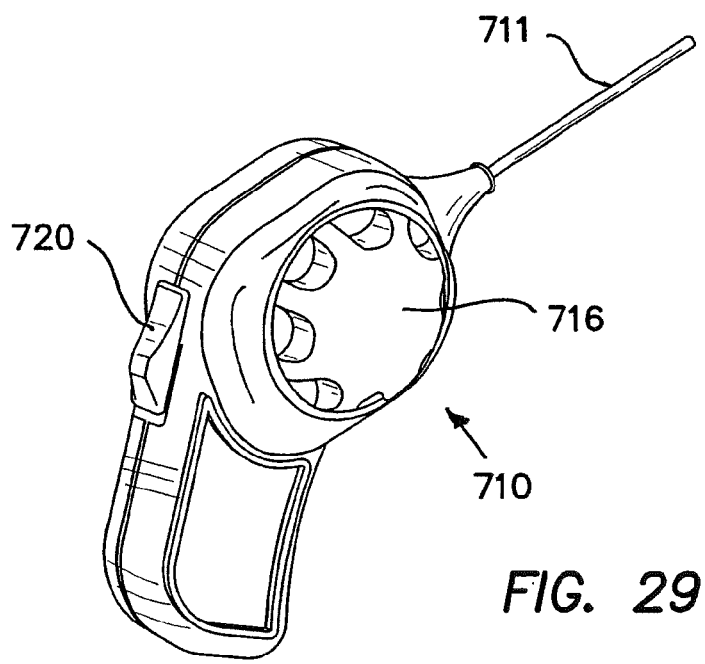
FIG. 29 illustrates a perspective view of an actuation hand-piece in accordance with one embodiment of the present invention.
Figure 30:
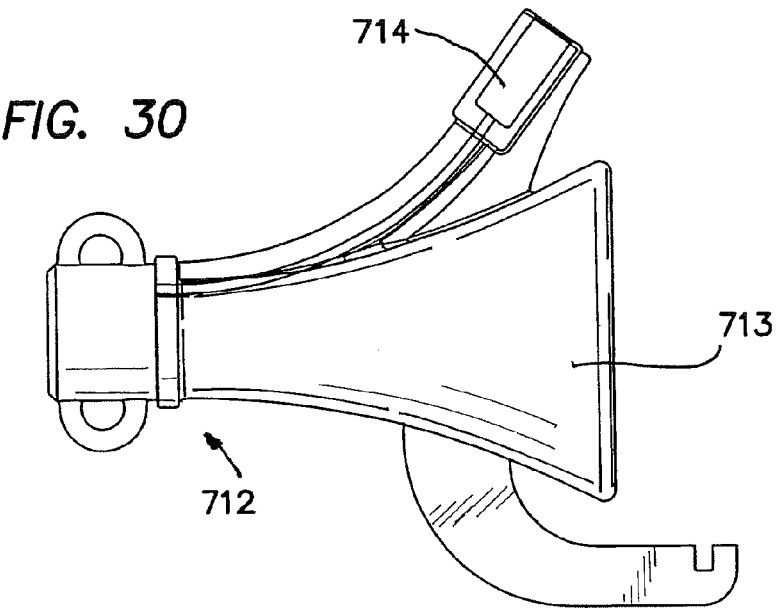
FIG. 30 illustrates a cross-sectional view of a connector in accordance with one embodiment of the present invention.
Figure 31:
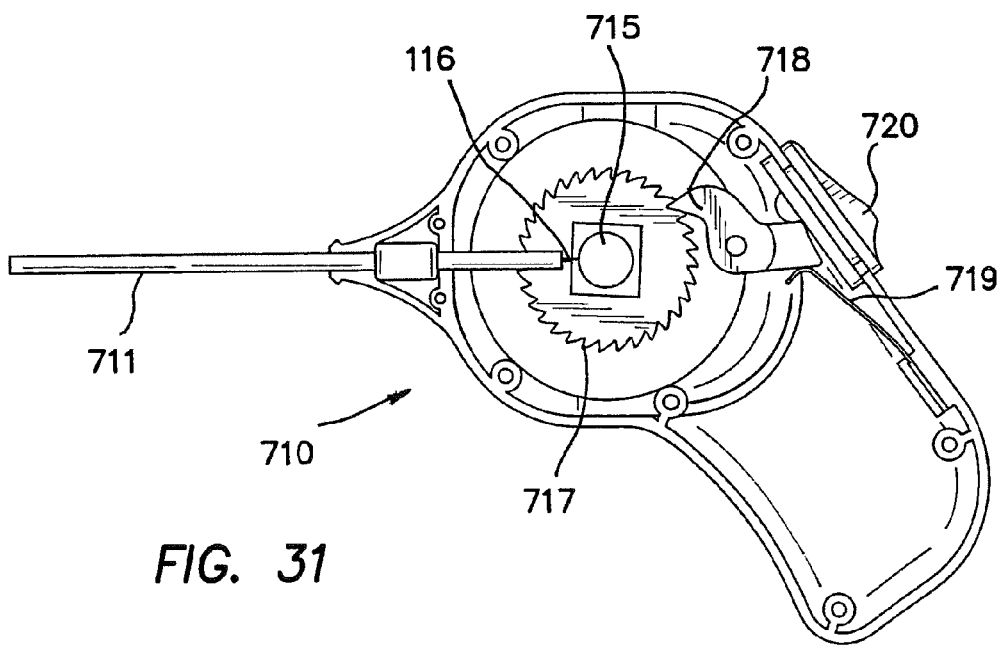
FIG. 31 illustrates a cross-sectional view of the actuation hand-piece of FIG. 29.

In FIGS. 29-31, one embodiment of an actuator or actuation hand-piece 710 of the present invention is remotely attached to an access sheath to control the tensioning and loosening of a tensioning device connected to the access sheath. As such, the actuator may be placed away from the surgical site or operating path or area so that the hand-piece does not prevent or interfere with the insertion of instruments along the working length of the access sheath. Additionally, the remote actuator does not occupy or add additional working space or length to the access sheath. Furthermore, another user may operate the actuator remotely allowing another user to focus on the surgical procedure, e.g., manipulating instruments to be or already inserted in the access sheath. Extended surgery time and confusion caused by switching between the actuator and other devices or simultaneously using the many devices may be reduced.

The actuator 710, in one embodiment, is connected to a flexible body or conduit 711, which is connected to the access sheath 102 via a Y-connector 712. The Y-connector 712 includes a funnel-shaped entry portion 713 that is sized and arranged to guide instruments into the primary lumen 112 of the access sheath 102. The Y-connector 712 also includes a channel 714 for connecting to the flexible conduit 711. The tensioning device 116 extends through the secondary lumen 114, channel 714, and flexible conduit 711 and is attached to an axle 715 disposed within the actuator 710. The axle 715 is connected to a dial or knob 716 that partially extends laterally from the hand-piece 710 with finger holds disposed radially throughout the knob 716. The other end of the axle 715 is rotatably connected to the hand-piece 710.

The knob 716 allows a user to control the tensioning device 116. For example, when rotated in one direction, e.g., clockwise, the tensioning device 116 is drawn proximally to wrap or wind around the axle 715. A plurality of teeth 717 radially disposed on the knob 716 within the hand-piece 710 or disposed on a separate or embedded ratchet wheel operatively engages with a corresponding lever or pawl 718. The pawl 718 pivoting about a post connected to the hand-piece 710 and biased by a leaf spring 719 engages with the teeth to permit rotational movement of the knob 716 in one direction, e.g., clockwise, while preventing rotational movement in the opposite direction. As such, as the knob 716 is rotated, incremental control of the deflection of the steerable portion 106 of the access sheath 102 is provided as the axle in the hand-piece 710 draws the tensioning device 116 proximally. A trigger 720 when actuated pivots the pawl 718 to disengage the pawl 718 from the teeth 717. As a result, the tensioning device 116 is allowed to unwind or move distally from the axle 715. Thus, the steerable portion 106 of the access sheath 102 straightens.

Figure 32A:
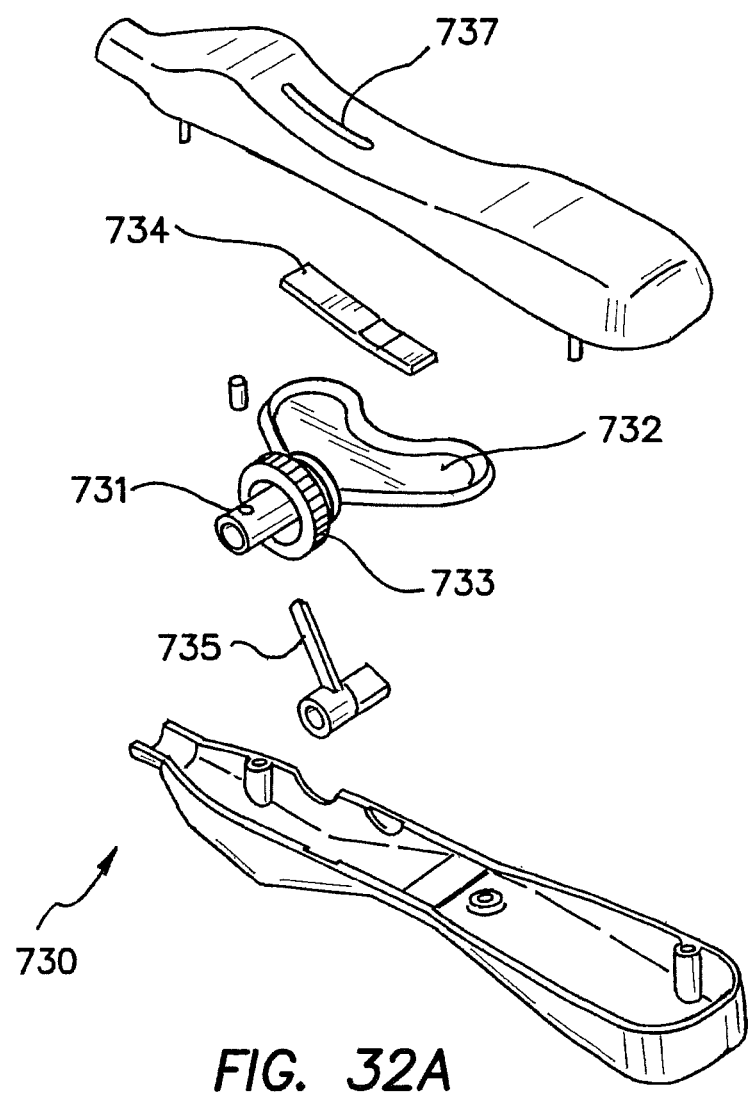
FIGS. 32A-B illustrate perspective views of a disassembled actuation hand-piece in accordance with one embodiment of the present invention.
Figure 32B:
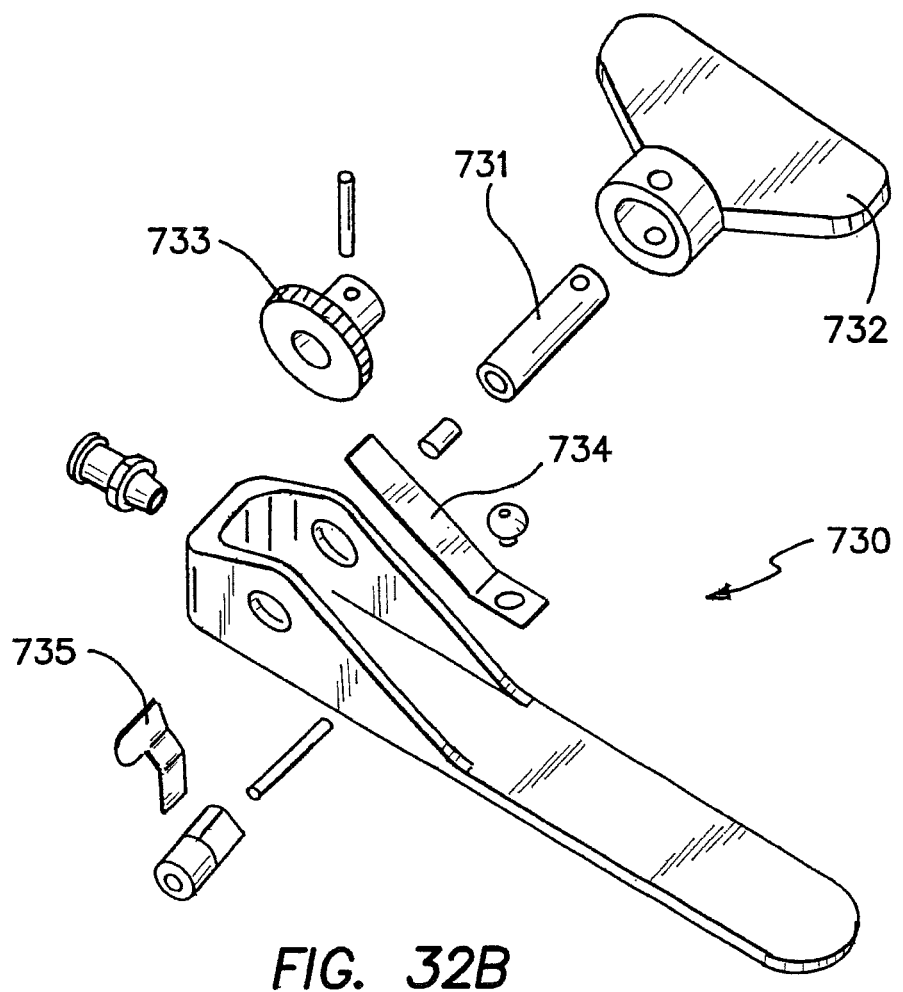
Figure 33A:
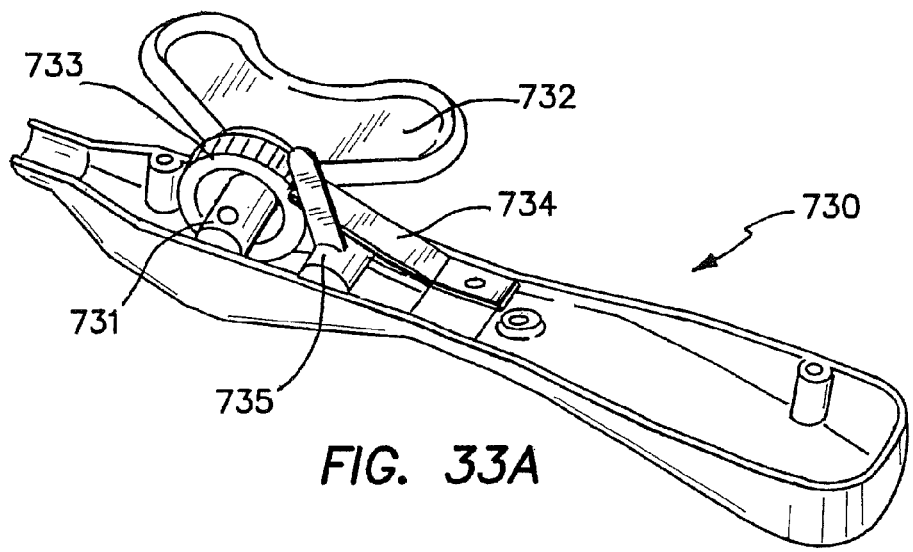
FIGS. 33A-B illustrate other perspective views of the disassembled actuation hand-piece of FIGS. 32 A-B.
Figure 33B:
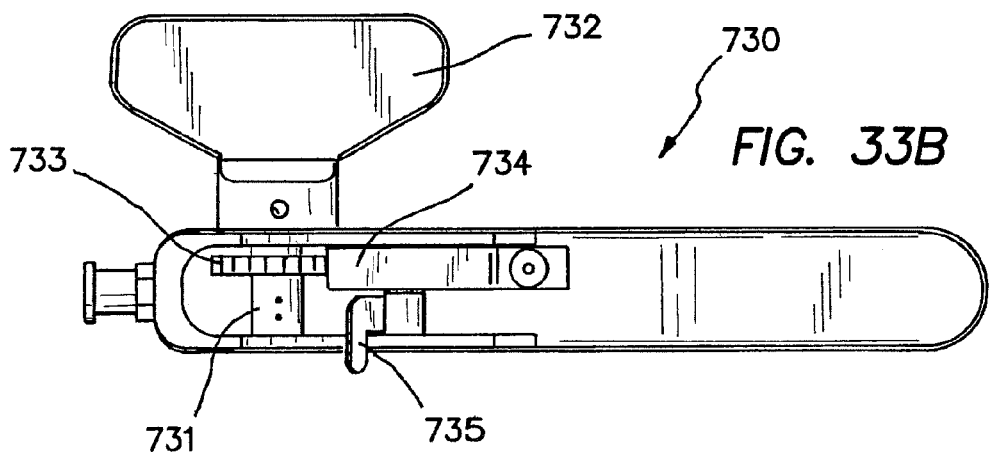
Figure 34:
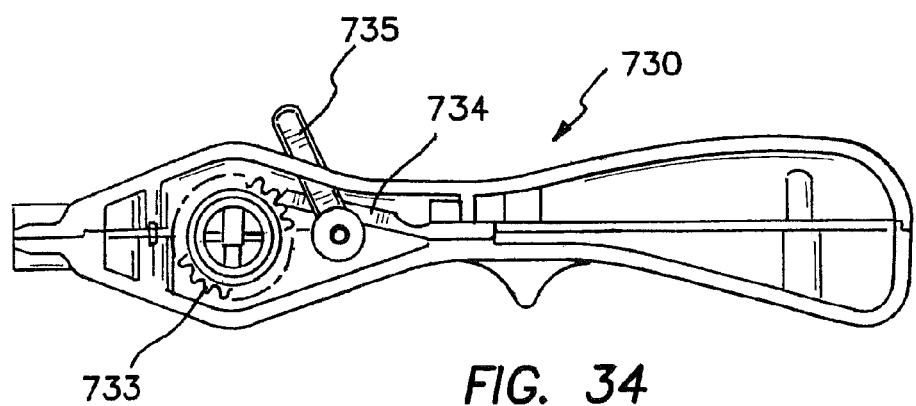
FIG. 34 illustrates a cross-sectional view of the actuation hand-piece of FIG. 32.
Figure 37:
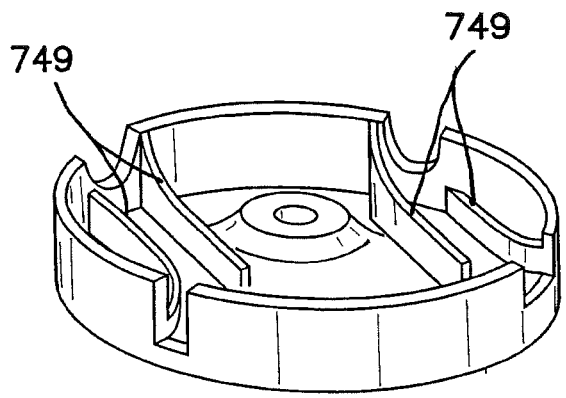
FIGS. 37-38 illustrate perspective views of embodiments of components of the actuation hand-piece of FIG. 35.
Figure 38:
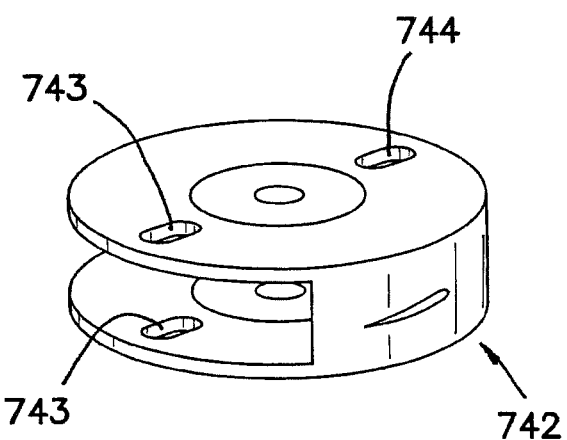

Referring now to FIGS. 32-34, another embodiment of an actuator or actuation hand-piece 730 of the present invention remotely attached to an access sheath 102 is shown. An axle 731 disposed within the hand-piece 730 is attached to the tensioning device 116. The axle 731 is also connected to a rotatable key or winged lever 732 extending laterally from one side of hand-piece 730.

The lever 732 allows a user to control the tensioning device 116. For instance, when rotated in one direction, e.g., clockwise, the tensioning device 116 is drawn proximally to wrap or wind around the axle 731 in the hand-piece 730. A plurality of teeth 733 radially disposed around the axle 731 or disposed on a ratchet wheel surrounding the axle operatively engages with a corresponding pawl or cantilever arm 734. The arm 734 mounted on the hand-piece 730 and engaged with the teeth 733 permit rotational movement of the lever 732 and axle 731 in one direction while preventing rotational movement in the opposite direction. This engagement provides incremental control of the tensioning device 116 and thus also of the steerable portion 106 of the access sheath 102.

The hand-piece 730 also includes a trigger lever 735 that is pivotally connected to a post in the hand-piece 730 and partially extends through a slot in the hand-piece 730. The lever 735 when actuated, e.g., pulled proximally, moves the cantilever arm 734 to disengage from the teeth 733 to allow the axle 731 to freely rotate. Therefore, the tensioning device 116 connected to the axle 731 unwinds and/or moves distally from the axle 731 causing the steerable portion 106 of the access sheath 102 to straighten.

In FIGS. 35-38, another embodiment of an actuator or actuation hand-piece 740 of the present invention that is remotely attached to an access sheath 102 to control the tensioning and loosening of the tensioning device 116 is shown. Disposed within the hand-piece 740 is an axle 741, which is attached to tensioning device 116. The axle 741 is connected to a slotted wheel 742 that is partially rotatable within the hand-piece 740. Generally opposing slots 743 and 744 are disposed in the slotted wheel through which respective dowels or pins 745 and 746 extend through and connect to distal ends of respective button arms 747 and 748. Proximal ends of button arms 747 and 748 extend through openings in the hand-piece 740.

Operationally, when the button arm 748 is lowered, the button arm 747 rises as the slotted wheel 742 rotates clockwise. As a result, the tensioning device 116 connected to axle 741 is not drawn to the hand-piece 740, such that the steerable portion 106 of the access sheath 102 is substantially straight. When button arm 747 is lowered, the button arm 748 rises and the slotted wheel 742 rotates causing the tensioning device 116 to be pulled by rotating axle 741 such that the steerable portion 106 of access sheath 102 deflects. In one aspect of the present invention, the hand-piece 740 includes guides 749 for aligning and guiding traversal of the button arms 747 and 748 and slots (not shown) for assisting linear movement of the pins 745 and 746 as the button arms move. The slotted wheel 742 also includes one or more openings along the circumference of the wheel to permit rotation of the wheel without interfering with the guides 749. In another aspect of the present invention, the axle 741 is connected to a screw knob for adjusting the tension or pre-winding the tensioning device 116 around the axle 741.

Figure 39:
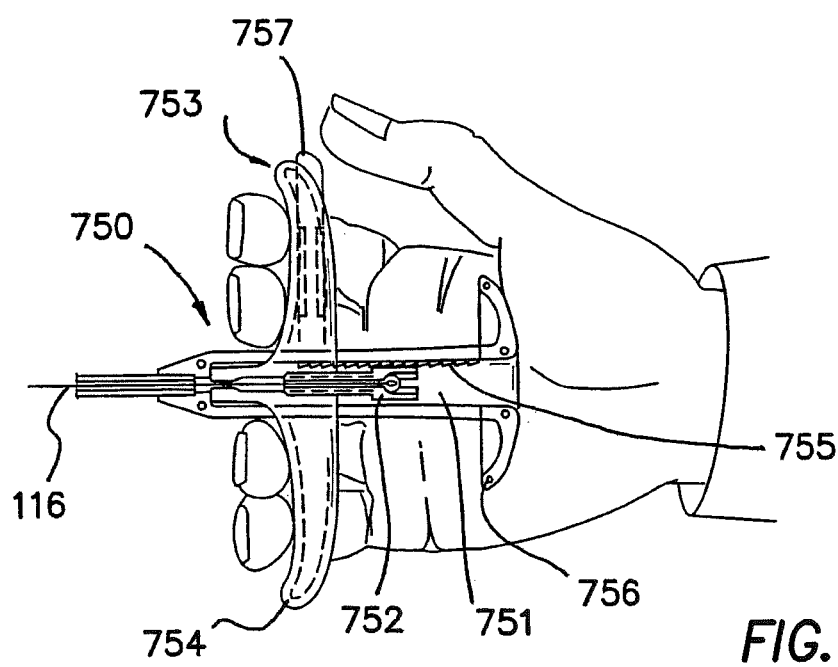
FIG. 39 illustrates a view of an actuation hand-piece in accordance with one embodiment of the present invention.

Referring now to FIG. 39, another embodiment of a remotely attached actuator or actuation hand-piece 750 is shown. In one aspect of the present invention, the hand-piece 750 fits within a user's hand in that a first closing motion moves a t-bar 753 proximally deflecting the access sheath 102 and an opening motion moves the t-bar 753 distally allowing the access sheath 102 to straighten. For example, the hand-piece 750 includes finger-extension members 754 to provide one or more fingers on each member 754 to grasp the t-bar 753. A distally flared end 756 of a tube 751 is also provided for resting in the palm of a hand.

Extending through a distal end of the tube 751 is the tensioning device 116 that attaches to plate 752 within the tube 751. The plate 752 is connected to the t-bar 753 that is slidably connected to tube 751. In one embodiment, an adjustment screw is connected to the t-bar 753 to adjust the location of the plate 752 relative to the t-bar 753 and within the tube 751. A set of teeth 755 within tube 751 operatively engages with a tooth or detent on t-bar 753 as the t-bar 753 moves.

With the t-bar 753 moving proximally, plate 751 also moves proximally thereby pulling tensioning device 116 to cause the steerable portion 106 of the access sheath 102 to deflect. Similarly, as the t-bar 753 and plate 751 moves distally, the tensioning device 116 loosens and thus the steerable portion 106 straightens. As such, this engagement provides incremental control of the deflection and/or straightening of the steerable portion 106 of the access sheath 102. A spring-loaded button 757 on one end of the t-bar 753, when actuated, disengages the tooth on t-bar 753 from the teeth 755 within tube 751 allowing the t-bar 753 to move freely.

Figure 40:
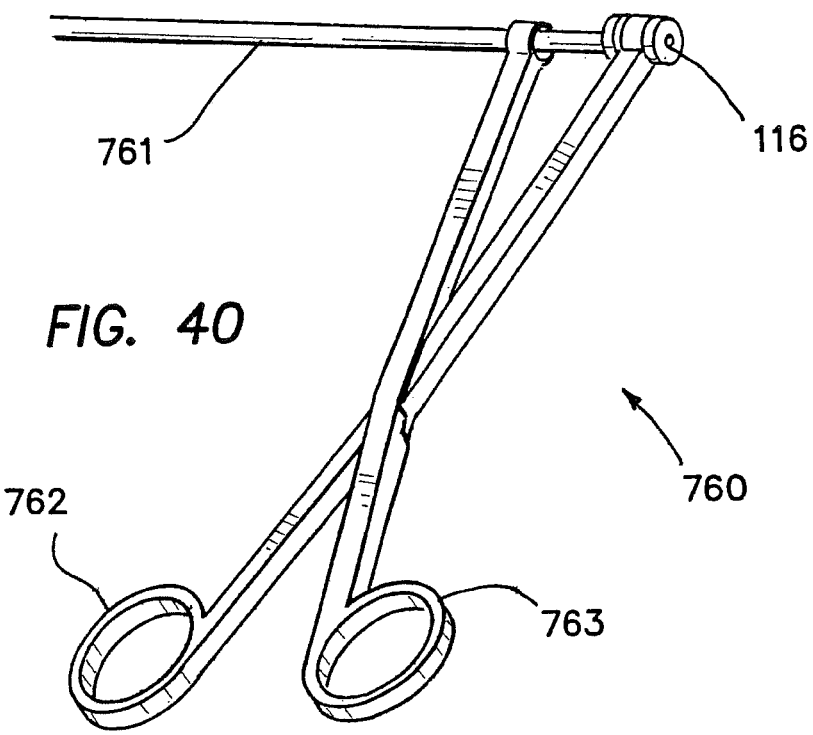
FIG. 40 illustrates a perspective view of an actuation hand-piece in accordance with one embodiment of the present invention.
Figure 41:
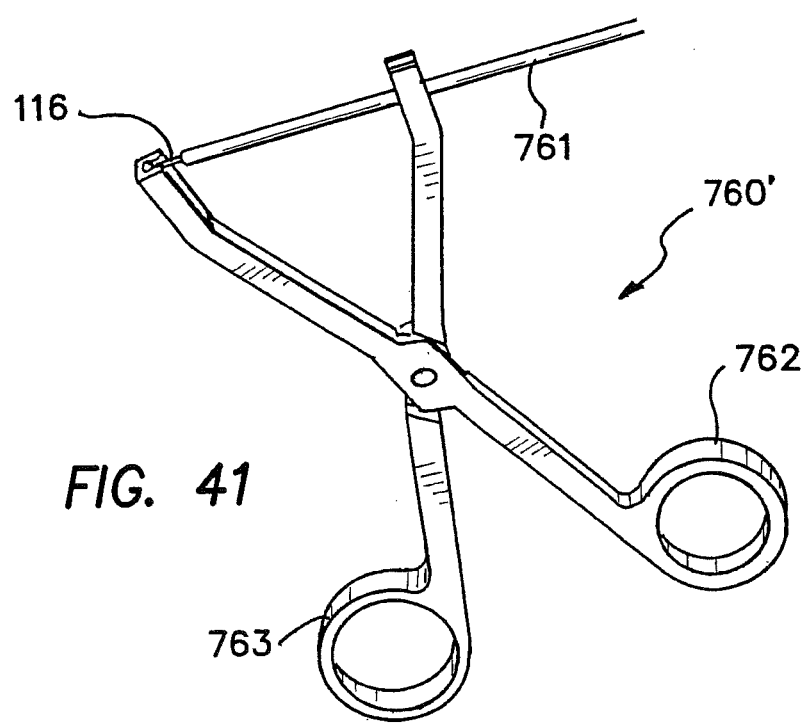
FIG. 41 illustrates a perspective view of an actuation hand-piece in accordance with one embodiment of the present invention.

FIGS. 40-41 illustrate another embodiment of the present invention of an actuator or actuation hand-piece 760 and 760' each remotely attachable to the access sheath 102. The hand-piece 760 and 760' are connected to a flexible body or tube 761 through which the tensioning device 116 extends. The tensioning device 116 is attached to a first handle member 762 that is pivotally connected to a second handle member 763. Actuation of the first handle member 762 allows a user to pull or release the tensioning device 116 to respectively deflect or straighten the steerable portion 106 of the access sheath 102. In one aspect of the present invention, a ratchet assembly is included to provide incremental control of the tensioning device 116 and thus the deflection of the steerable portion 106 of the access sheath 102.

It is appreciated that the access sheath may comprise a plurality of pull wires attached to a plurality of thumbwheels, axles, knobs or other types of movable components of an actuation hand-piece to deflect the steerable portion of the sheath in different directions. Also, it is appreciated that the tensioning device may be hydraulic, pneumatic or electronic in nature and the actuation hand-piece may instead be foot, finger or otherwise sensor actuated and may include corresponding foot, finger or otherwise sensor extensions.

Figure 42A:
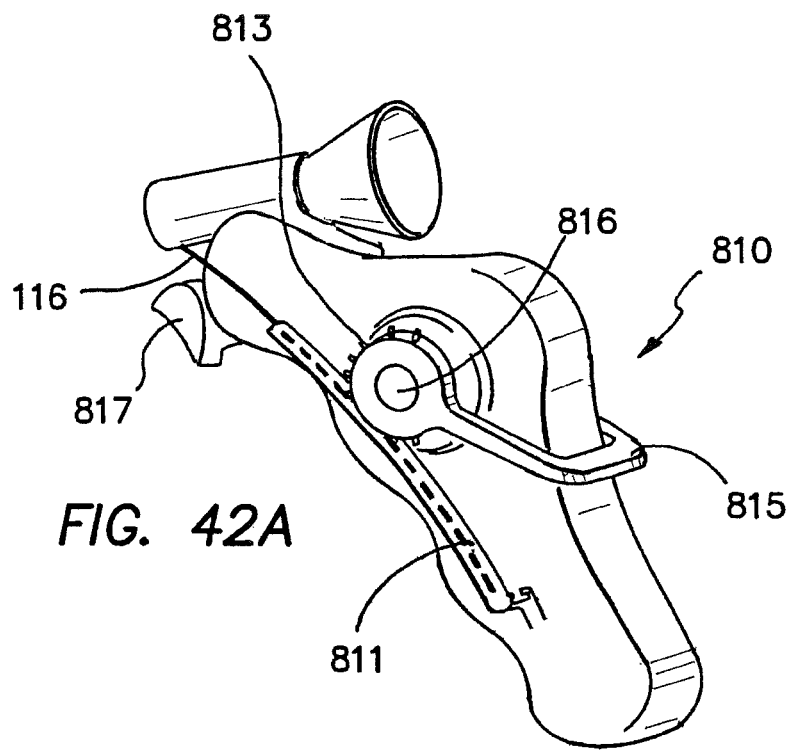
FIG. 42A illustrates a perspective view of an actuation hand-piece in accordance with one embodiment of the present invention.
Figure 42B:
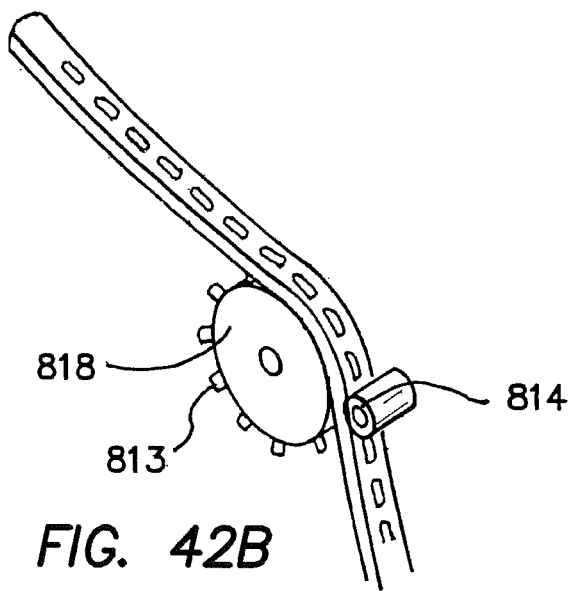
FIG. 42B illustrates a perspective view of one embodiment of components of the actuation hand-piece of FIG. 42A.
Figure 43:
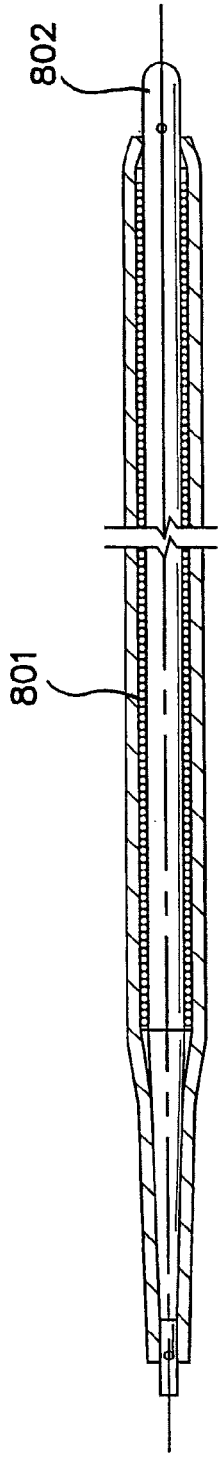
Figure 44:
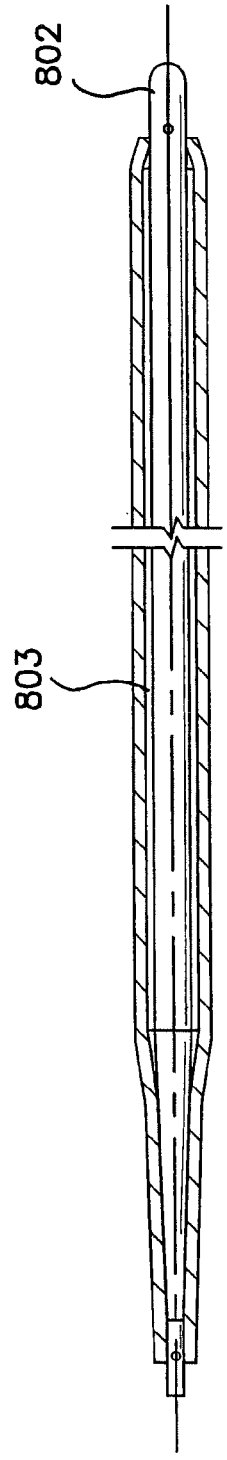
Figure 45:
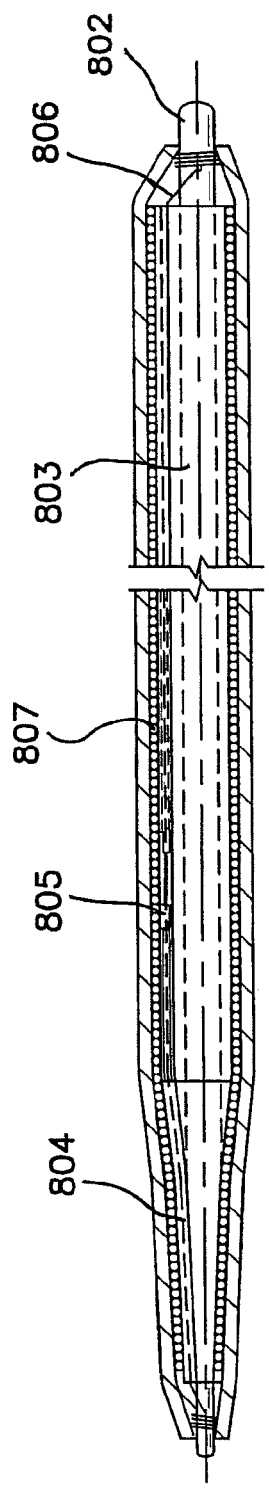

In various embodiments, for example, the embodiments previously described and/or the embodiment of an actuation hand-piece 810 shown in FIGS. 42A-B, the tensioning device 116 is connected to a belt 811. The belt 811 acts as an intermediary between the tensioning device 116 and a movable component 818 in the hand-piece 810. The movable component may also be, for example, slider 514 or 614 (FIGS. 18B and 24), cylinder 526 (FIG. 20), movable handle member 622 (FIG. 26), axle 715 or 731 (FIGS. 31 and 32), and various other movable components fully or partially disposed within or otherwise part of an actuator or hand-piece which is connectable to the tensioning device 116. Through belt 811, stress or forces that may be applied by or result from the movable component 818 is displaced from the tensioning device 116. Therefore, stress experienced by the tensioning device 116 caused by the actuation of the hand-piece may be reduced.

The belt 811 includes a number of apertures 812 for engaging teeth 813 radially disposed on the movable component 818 of the hand-piece 810. In one embodiment, the belt 811 includes teeth or protrusions for engaging corresponding apertures, teeth or protrusions of the movable component 818. With either engagement, incremental control of the tensioning device 116 is provided. As such, the belt 811 draws the tensioning device 116 proximally as the knob is rotated in one direction and rotating the knob in the opposite direction, allows the tensioning device to withdraw from the hand-piece 810.

A pin or roller 814 may also be included to assist in the engagement of the belt 811 with a movable component 818 of the hand-piece 810. In one aspect of the present invention, the belt 811 is pliable. In another embodiment, a plate, bar, or a less flexible component may be connected to the belt 811 for drawing or releasing the belt 811 in conjunction with or without the movable component 818.

A u-shaped lever 815 is connected to a knob 816 that is disposed on one or both sides of the hand-piece 810 and is connected to the movable component 818 in the hand-piece 810. Through actuation of the u-shaped lever 815, a user can control the movement/tension of the tensioning device 116 and thus the deflection and straightening of the steerable portion 106 of the access sheath 102. In one embodiment, a plate is connected to the u-shaped lever 815 and the belt 811 to draw and release the tensioning device 116.

In one aspect of the present invention, a trigger 817, when actuated, locks the belt 811, the movable component 818 or the u-shaped lever 815, thus preventing further movement of the tensioning device 116 and the deflection/straightening of the steerable portion 106 of the access sheath 102. Alternatively, the trigger 817 releases or disengages control of the tensioning device 116 from the belt 811, the movable component 818 or the u-shaped lever 815 to allow the tensioning device 116 to return to its original position or state.

Referring now to FIGS. 43-46, embodiments of an access sheath in various stages of fabrication is shown. A wire 801 is wound around a support member or mandrel 802 in which the size and shape of mandrel generally defines the size and shape of primary lumen 112 of the access sheath 102. The mandrel, in one embodiment, is stainless steel and made of or is coated with a low friction material or surface, e.g., Teflon or various mold releases, allowing for the mandrel to be easily removed from the access sheath 102. The wire 801 is wound in an over counter fashion by using anchors or starting and stopping points substantially orthogonal of each other and thus winding the wire 801 in an oblique line along mandrel 802. As such, the wire 801 is wound such that the wire's tendency to unwind is counteracted. In one embodiment, prior to the addition of the wire 801, the mandrel 802 is coated with or inserted into a plastic or PVC material tube to allow instruments and the like to be smoothly inserted into the primary lumen without interference from the wire 801.

The wire 801, in one embodiment, is a plastic coated wire and particularly, a stainless steel co-extruded wire with an approximate diameter of 0.006 inches fused, coated or otherwise included with a plastic material to make the total diameter of the wire 801 to be about 0.012 inches. The mandrel 802 including wire 801 is placed into or inserted into a control tube. Air, in one embodiment, is supplied, e.g., at 100 PSI, on the opposite end of insertion to assist insertion of the mandrel 802 by expanding the control tube. The control tube, in one embodiment, may be made of silicon or a material with a higher melting point than the plastic coating of wire 801. This assembly is then heated such that the plastic coating of wire 801 melts and adheres to itself to form a generally continuous tubular structure or major tube 803. The control tube is then removed.

A minor tube 804 is placed on or included with the major tube 803. The minor tube 804 is longer than the major tube 803 and thus extends substantially further along the mandrel 802 than the major tube 803. Extending within a portion of the minor tube 804 is a generally tubular structure or inner tube 805 that is about as long as the major tube 803. In one embodiment, the inner tube 805 is made of polyimide and the minor tube 804 is made of carbothane that when heated adheres to the inner tube 805, the major tube 803 and other portions of the access sheath, which are described below, that surrounds the outer periphery of the minor tube 804.

The inner tube 805 within the minor tube 804 is adapted to receive the support wire 806. The size and shape of the support wire 806 along with the inner tube 805 generally defines the size and shape of the secondary lumen 114 of the access sheath 102. In one embodiment, the support wire is a stainless steel wire with a diameter of about 0.12 inches. The support wire 806 is secured to a proximal end of the mandrel 802, threaded through the inner tube 805 and the minor tube 804 and secured to the distal end of the mandrel 802. In one embodiment, the support wire 806 secures the minor tube 804 to the major tube 803.

The minor tube 804 extends along the mandrel 802 substantially more than the inner tube 805. In other words, the length of the minor tube 804 is longer than the inner tube 805. The minor tube 804 is also more flexible than the inner tube 805. As such, the portion from the end point of the inner tube 805 and/or the major tube 803 to near the end point of the minor tube 804 eventually defines the steerable portion 106 of the access sheath 102. In one embodiment, the minor tube 804 is shorter and less flexible than the inner tube 805. Thus, in this embodiment, the portion from the end point of the minor tube 804 and/or the major tube 803 to near the end point of the inner tube 805 eventually defines the steerable portion 106 of the access sheath 102.

In one embodiment, the minor tube 804, inner tube 805 and the major tube 803 are placed into a final tube to enclose the minor tube 804 and inner tube 805 between the major tube 803 and the final tube. This assembly is placed into or inserted into a control tube such that the assembly adheres or bonds together and then the control tube is removed.

In one embodiment, the minor tube 804 or the inner tube 805, whichever extends further, is rigid, e.g., a stainless steel tube, to assist in the deflection of the steerable region 106. As such, the rigidity of the minor tube 804 or inner tube 804 prevents the non-steerable portion of the access sheath 102 from bowing. As such, the tube shifts the force caused by the tensioning device 116 to deflect the steerable region directly towards or at the steerable region 106. Also, a rigid secondary lumen formed by the rigid tube may assist in the protection of the tensioning device and instruments inserted or withdrawn from the primary lumen.

A wire 807 is wound around the minor tube 804, the inner tube 805 and the major tube 803. In one embodiment, where the final tube is utilized, the wire 807 is also wound around the final tube. In one embodiment, the wire 807 is similar in construction or composition as that of wire 801 and/or extends slightly beyond the distal end of the minor tube 804 or inner tube 805.

A support tip, in one embodiment, is placed on a distal end or slightly beyond the distal end of the wire 807 to assist in securing the wire 807 around the minor tube 804 or inner tube 805 and/or to provide an atraumatic tip. The support tip may be a 75 Shore D material. The mandrel 802 with rest of the assembly is inserted into a control tube. As previously mentioned, air, in one embodiment, is supplied on the opposite end of insertion to assist insertion of the mandrel 802 by expanding the control tube. In one aspect, a support tube is used to temporarily encompass the control tube when the tube is pressurized in the event the tube breaks down. The control tube with the assembly is heated such that the plastic coating of wire 807 melts and adheres to itself to form a generally continuous tubular structure or tube 808. The control tube is then removed. In one embodiment, the control tube and assembly are heated at around 165 degrees plus or minus about five to ten degrees for about ten to fifteen minutes. As such, an access sheath 102 with a variable flexibility is created.

The support wire 806 is disconnected from the mandrel 802. For example, the support wire 806 on the distal end of the mandrel 802 is cut and then the mandrel 802 is withdrawn from the access sheath 803. At or near the tip of the access sheath, a tensioning device, e.g., a pull wire, is attached and threaded to the minor tube 804 and inner tube 805 out the proximal end of the access sheath 102 for securing to an actuator. As such, the access sheath is deflectable and controllable.

In one embodiment, the tensioning device is knotted or looped around an opening or cut in the access sheath, the support tip and/or between loops in the wire 807 and back through itself. A catch wire threaded through the inner tube 805 and the minor tube 804 hooks or otherwise attaches to the tensioning device. The catch wire is removed out the proximal end of the access sheath thereby threading the tensioning device through and out the proximal end of the access sheath 102. As it is appreciated the support wire 806 has a diameter sufficiently larger than the diameter of the tensioning device, the catch wire or loops and hooks of the catch wire to permit easy passage of these devices through the secondary lumen of the access sheath 102. A secondary support tip, in one embodiment, is placed on the distal end of the access sheath 102 to assist in securing the tensioning device to the access sheath and/or to provide an atraumatic tip.

As shown in FIGS. 46A-C, the distal end 809a of the access sheath 102 is tapered and thus has a smaller diameter than the proximal end 809b of the access sheath 803. The primary lumen 112 and secondary lumen 114 diameters, however, remain substantially constant throughout the access sheath 102. Additionally, the tapering or reduced diameter of the access sheath is a result of the halting or non-extension of the inner tube 805 or minor tube 804, in one embodiment, and the major tube 803 along the length of the mandrel 802. As a result, the steerable portion 106 includes a reduced amount of materials and more flexible materials, and thus the steerable portion is easily deflected, bent, shaped or curved in response to the manipulation of the attached tensioning device while the other portion of the access sheath 102, including more material and less flexible material, remains substantially fixed, e.g., straight and substantially in the same plane, preventing any inadvertent or unintended movement of the access sheath.

Additionally, since the steerable region 106 of the access sheath 102 is reinforced by wire 807, the steerable region 106 is strengthen such that a flexible, pre-bendable or otherwise not actively controllable instrument may be controllably deflected dynamically as the steerable region 106 is controlled. Additionally, an actively deflectable surgical instrument may have a complicated construction providing components, e.g., optics or clamps, to perform its surgical function and components to perform the active deflection. Therefore, such instruments may be fragile or if broken may be expensive to replace or repair or still usable as a surgical instrument but not actively deflectable. As such, the strengthen steerable region 106 may replace the components or use of the components in such surgical instruments or induce an broken instrument to be controllably deflected thereby reducing replacement, repair and/or construction costs, reducing wear and tear of such instruments and increasing the life of such instruments. Also, the reinforced access sheath 102 through wire 807 and/or wire 801 allows the size and shape of the primary lumen to remain substantially constant throughout the access sheath 102, thereby reducing forces on instruments placed within the access sheath which may extend the life of these instruments.

The forces or stress accumulated along the access sheath that may cause kinks in the access sheath are also distributed along the access sheath due to the composite construction of the access sheath described above and are further counteracted by the wire coils, e.g., wire 807 and 803. Thus, kinks in the access sheath are reduced. The wire coils also allow the access sheath walls to be very thin without reducing durability or strength in the access sheath. Thus, the overall or outer diameter of the access sheath may be small, which may also reduce the incision or insertion point for the access sheath, without reducing the size or diameter of the primary lumen. As such, the access sheath of various embodiments of the present invention has thin walled portions, a large lumen, an atraumatic end, and a kink resistant construction and is strong, stiff and yet flexible enough to be intricately guided through the body cavity or tissue. In one embodiment, the wire coils are wound in a multifilar fashion with materials having alternating durometers.

Various other examples of processes that may be used to manufacture the access sheath 102 or portions of the access sheath 102 are described in U.S. patent application Ser. Nos. 10/766,138 and 10/298,116, the disclosures of which are hereby incorporated by reference. It is appreciated that these processes or portions of the processes may be varied or combined with the previously described process and vice versa. For example, various ring-shaped elements, such as, plastic rings, metallic rings, un-reinforced plastic rings and metal reinforced plastic rings, and the like may be utilized instead of or in addition to the wires 803 and/or 807. Additionally, a separate mandrel may be utilized to separately form or define the primary and secondary lumens and combined to make the access sheath.

In one embodiment of the present invention, various embodiments of access sheaths and actuators previously described, here now referred to as the access sheath, combined with an instrument or device used to stretch or enlarge an opening, e.g., a dilator, allows for gradual and atraumatic dilation of the ureter while being placed. Once the access sheath has been placed at a desired location, the dilator is removed and the access sheath is left in place. The access sheath allows for continued access to the desired area, for example, for the placement of an ureteroscope and other therapeutic instruments, while providing protection of the ureter. For instance, the access sheath may protect the ureter during the placement and removal of devices within the access sheath, during the removal of stone fragments or other tissue, and during the removal of a potentially cancerous biopsy specimen.

Additionally, with the access sheath being deflectable or steerable, an urologist may effectively and efficiently locate stones and stone fragments within the kidney. When a stone burden is found in one of the calyces of the kidney, especially in the lower pole portion of the kidney; it may be difficult for the urologist to continue to go back to the same calyx or location to remove the burden.

When there are many fragments within a calyx, many entries and exits may be performed to remove the burden. Also, when a stone or stone fragment is removed, the instruments and tissue, e.g., the scope and stone basket (with the stone or stone fragment) are removed as a single unit. The scope is then passed back through the sheath and manipulated to find the same calyx in order to remove the remaining burden. However, with the access sheath 102, the access sheath can be left deflected in place looking at the same calyx or location, while the scope and stone basket are removed. As a result, the urologist's procedure time may be reduced, as the urologist may not have to manipulate the ureteroscope to look for the same calyx each time. The amount of time saved may be significant, especially if there is a large stone burden within the kidney. Additionally, the likelihood of doing damage to the kidney due to the additional manipulation that takes place every time the ureteroscope is placed back into the kidney may be reduced. Thus, with the access sheath, one can keep the sheath deflected towards a particular calyx and remove the stone burden without having to find the calyx each and every time a fragment is removed.

When the urologist manipulates an ureteroscope, the urologist may sometimes use the inside walls of the kidney to help deflect the ureteroscope to enter into a particular difficult locale. With the access sheath 102, instead of using the inside wall to help deflect the ureteroscope the access sheath may be used. Also, as previously mentioned, this will also help reduce the "wear and tear" on surgical instruments, such as ureteroscopes. The deflecting mechanism with the ureteroscope, if provided, can be damaged often and expensive repair. The use of the access sheath may reduce the damage to the ureteroscope when it is used to help manipulate the ureteroscope to desired locations within the kidney.

The use of the access sheath 102 may also help a lesser-experienced urologist perform the same difficult procedure as their more experienced colleagues. In performing this procedure, the urologist may access the lower pole of the kidney in order to remove a stone burden. By performing this procedure in a retrograde fashion, one can reduce a patient's recovery time. If an urologist were neither skilled nor comfortable with using an ureteroscope in a retrograde fashion to remove a stone burden from a kidney's lower pole, the urologist would typically approach the stone burden in an antegrade fashion. This places a sheath percutaneously and thus may add additional recovery time for a patient as well as potentially increasing morbidity. But, with the access sheath 102 and an ureteroscope, an urologist may efficiently and effectively locate and remove a stone burden within the lower pole of a kidney. The access sheath can also be used in an antegrade fashion and will provide the same or similar features described above, however access in this manner may not be the preferred method.

Accordingly, the present invention provides a steerable kink resistant access device. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

We claim:

1. A surgical access device comprising:
   a tube having a substantially rigid portion and a substantially flexible portion extending from the substantially rigid portion, the tube including a primary lumen and a secondary lumen both extending through the tube, the secondary lumen having a tensioning device extending through the secondary lumen and connected to the flexible portion;
   a Y-connector having a distal end connected to the tube and a proximal end including a funnel-shaped portion, the tensioning device extending through the connector from the distal end toward the proximal end;
   a flexible tubing connected to the Y-connector through which the tensioning device extends;
   a handle connected to the flexible tubing and including an axle disposed within the handle and a knob connected to and outside the handle, the axle connected to the tensioning device and the knob such that rotation of the knob in one direction draws the tensioning device proximally around the axle to deflect the tube;
   a pawl connected to the handle;
   a trigger connected to the handle and the pawl; and
   a set of teeth connected to the axle and operatively engaging with the pawl;
   wherein the trigger when actuated causes the pawl to move to disengage the pawl from the teeth such that the tensioning device is allowed to move distally to straighten the tube.

2. The surgical access device of claim 1, further comprising finger holds disposed radially throughout the knob.

3. The surgical access device of claim 1, wherein the trigger comprises a button slidable between a first position and a second position;
   wherein the trigger, when disposed in the first position, causes the pawl to move to engage the pawl with the teeth and wherein the trigger, when disposed in the second position, causes the pawl to move to disengage the pawl from the teeth.

4. The surgical access device of claim 1, wherein the tensioning device is at least one pull wire.

5. The surgical access device of claim 1, wherein the handle further comprises a directional indicator.

6. The surgical access device of claim 1, wherein the tube comprises an inner plastic body, a spring coil and an outer plastic body.

7. The surgical access device of claim 6, wherein the inner plastic body is surrounded by the spring coil and covered by the outer plastic body.

8. The surgical access device of claim 1, wherein the flexible portion includes a weakened region extending along the flexible portion.

9. The surgical access device of claim 1, wherein the flexible portion includes slots extending along the flexible portion and slits extending along the flexible portion on a generally opposing side of the slots, the slots being larger than the slits.

10. The surgical access device of claim 1 wherein the funnel-shaped portion is sized and configured to guide instruments into the primary lumen.

11. The surgical access device of claim 1 wherein the Y-connector includes a channel for connecting to the flexible portion.

12. The surgical access device of claim 1 wherein the knob extends laterally from the handle.

13. The surgical access device of claim 1 further including a leaf spring connected to the handle; wherein the pawl is biased by the leaf spring and engages with the teeth to permit rotational movement of the knob in one direction while preventing rotation movement in the opposite direction.

14. The surgical access device of claim 13 wherein, as the knob is rotated, incremental control of the deflection of the tube is provided.

15. A surgical access device comprising:
   a tube having a substantially rigid portion having a first diameter and a substantially flexible portion having a second diameter and extending from the substantially rigid portion, the first diameter being smaller than the second diameter, the tube including a primary lumen and a secondary lumen both extending through the tube, the secondary lumen having a pull wire extending through the secondary lumen and connected to the flexible portion of the elongated body;

a connector having a distal end connected to the tube and a proximal end including a funnel-shaped portion, the pull wire extending through the connector from the distal end to the proximal end;

a plastic tubing connected to the connector through which the pull wire extends through;

a handle connected to the plastic tubing and including an axle disposed within the handle and a knob connected to and outside the handle, the axle connected to the pull wire and the knob such that rotation of the knob in one direction draws the pull wire proximally around the axle to deflect the tube;

a pawl connected to the handle;

a trigger connected to the handle and the pawl; and a first set of teeth connected to the axle and operatively engaging with the pawl;

wherein the trigger when actuated causes the pawl to move to disengage the pawl from the first set of teeth such that the pull wire is allowed to move distally to straighten the tube.

16. The surgical access device of claim 15 wherein the funnel-shaped portion is sized and configured to guide instruments into the primary lumen.

17. The surgical access device of claim 15 wherein the connector includes a channel for connecting to the flexible portion.

18. The surgical access device of claim 15 wherein the knob extends laterally from the handle.

19. The surgical access device of claim 15 further including a leaf spring connected to the handle; wherein the pawl is biased by the leaf spring and engages with the teeth to permit rotational movement of the knob in one direction while preventing rotation movement in the opposite direction.

20. The surgical access device of claim 15 wherein, as the knob is rotated, incremental control of the deflection of the tube is provided.

* * * * *

UNITED STATES PATENT AND TRADEMARK OFFICE
CERTIFICATE OF CORRECTION

| | | |
|---|---|---|
| PATENT NO. | : 9,675,378 B2 | Page 1 of 1 |
| APPLICATION NO. | : 14/164954 | |
| DATED | : June 13, 2017 | |
| INVENTOR(S) | : Charles C. Hart et al. | |

It is certified that error appears in the above-identified patent and that said Letters Patent is hereby corrected as shown below:

In the Specification

Column 17, Line 50: Please delete "strengthen" and add --strengthened--

Column 17, Line 60: Please delete "strengthen" and add --strengthened--

Column 17, Line 62: Please delete "an" and add --a-- after induce

In the Claims

Column 22, Line 8: Please add a --Y-connector-- after wherein the

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*